United States Patent [19]

Demorest et al.

[11] Patent Number: 5,264,101
[45] Date of Patent: Nov. 23, 1993

[54] CAPILLARY ELECTROPHORESIS MOLECULAR WEIGHT SEPARATION OF BIOMOLECULES USING A POLYMER-CONTAINING SOLUTION

[75] Inventors: David M. Demorest, Scotts Valley; William E. Werner, San Carlos; John E. Wiktorowicz, San Jose, all of Calif.

[73] Assignee: Applied Biosystems, Inc., Foster City, Calif.

[21] Appl. No.: 877,956

[22] Filed: May 1, 1992

Related U.S. Application Data

[63] Continuation-in-part of Ser. No. 682,582, Apr. 8, 1991, Pat. No. 5,181,999, which is a continuation of Ser. No. 432,061, Nov. 6, 1989, Pat. No. 5,015,350.

[51] Int. Cl.$^5$ .................. G01N 27/26; G01N 27/447
[52] U.S. Cl. ....................... 204/299 R; 204/180.1; 204/182.8
[58] Field of Search ............. 204/180.1, 299 R, 182.8

[56] References Cited

U.S. PATENT DOCUMENTS

| | | | |
|---|---|---|---|
| 4,405,798 | 9/1983 | Hall et al. | 549/363 |
| 4,657,656 | 4/1987 | Ogawa | 204/299 R |
| 4,690,749 | 9/1987 | Van Alstine et al. | 204/299 R |
| 4,891,119 | 1/1990 | Ogawa | 204/299 R |
| 4,931,328 | 6/1990 | Swedberg | 428/36.91 |
| 4,997,537 | 3/1991 | Karger et al. | 204/299 R X |
| 5,069,766 | 12/1991 | Zhu et al. | 204/180.1 |

FOREIGN PATENT DOCUMENTS

0417925A2 8/1990 European Pat. Off.
0442177A1 8/2191 European Pat. Off.

OTHER PUBLICATIONS

Alexandra Widhalm "Capillary zone electrophoresis with a linear, non-cross-linked polyacrylamide gel:-separation of proteins according to molecular mass" Journal of Chromatography 549 (1991) 446-451.

Toshio Takagi et al "Application of schlieren optics to real-time monitoring of protein electrophoresis in crosslinker-free linear polyacrylamide solution" Electrophoresis 1991, 12, 436-438.

Bode, H.-J., "The Use of Liquid Polyacrylamide in Electrophoresis. I. Mixed Gels Composed of Agar-Agar and Liquid Polyacrylamide," Anal. Biochem. 83:204-210 (1977).

Bode, H.-J., "The Use of Liquid Polyacrylamide in Electrophoresis. II. Relationship between Gel Viscosity and Molecular Sieving," Anal. Biochem. 83:364-371 (1977).

Bode, H.-J., "The Use of Liquid Polyacrylamide in Electrophoresis: III. Properties of Liquid Polyacrylamide in the Presence of Cellulose Acetate," Anal. Biochem. 92:99-110 (1979).

Bode, H.-J., "Size Fractionation of Protein-Dodecylsulfate Complexes by Liquid Polyacrylamide Contained in Capillary Spaces between Glass Beads," Hoppe-Seyler's Z. Physiol. Chem. 359:1237-1238 (1978).

Bode, H.-J., "SDS—Polyethyleneglycol Electrphoresis: A Possible Alternative to SDS—Polyacrylamide Gel Electrophoresis," FEBS Letters 65 (1):56-58 (1976).

Chin, A. A.: and Colburn, J. C., "Counter-migration capillary electrophoresis (CMCE) in DNA restriction (List continued on next page.)

Primary Examiner—John Niebling
Assistant Examiner—John S. Starsiak, Jr.
Attorney, Agent, or Firm—Gary R. Fabian; Peter J. Dehlinger

[57] ABSTRACT

A capillary tube with a charged inner surface for use in capillary electrophoresis and methods. The tube is filled with an electrolyte solution containing 0.05-30% weight/weight of a hydrophilic polymer which is characterized by (A) a molecular weight of 20-5,000 kilodaltons, and (B) a charge between 0.01 and 1.0% as measured by the molar percent of charged monomer subunits to the total polymer subunits, where said charged monomer subunits have the charge opposite to the wall charge at a selected electrophoresis pH.

31 Claims, 10 Drawing Sheets

OTHER PUBLICATIONS fragment analysis," Am. Biotech. Lab./News Edition 7 (10A):16 (1989).

Gordon, M. J., et al., "Protocol for Resolving Protein Mixtures in Capillary Zone Electrophoresis," Anal. Chem. 63:69–72 (1991).

Hjerten, S., et al., "High-Performance Electrophoresis of Acidic and Basic Low-Molecular-Weight Compounds and of Proteins in the Presence of Polymers and Neutral Surfactants," J. Liquid Chromatogr. 12 (13):2471–2499 (1989).

Horowitz, P. M., et al., "Electrophoresis of Proteins and Nucleic Acids on Acrylamide-Agarose Gels Lacking Covalent Crosslinking," Anal. Biochem. 143:333–340 (1984).

Johansson, B. G., and Hjerten, S., "Electrophoresis, Crossed Immunoelectrophoresis, and Isoelectric Focusing in Agarose Gels with Reduced Electroendosmotic Flow," Anal. Biochem. 59:200–213 (1974).

Langevin, D., and Rondelez, F., "Sedimentation of large colloidal particles through semidilute polymer solutions," Polymer 19:875 (1978).

Mazzeo, J. R., and Krull, I. S., "Capillary Isoelectric Focusing of Proteins in Uncoated Fused-Silica Capillaries Using Polymeric Additives," Anal. Chem. 63:2852–2857 (1991).

Nordt, F. J., et al., "Elimination of Electroosmotic Flow in Analytical Particle Electrophoresis," in *Hydrogels for Medical and Related Applications*, J. D. Andrade, ed., pp. 225–240 (1976).

Takagi, T., et al., "Application of schlieren optics to real-time monitoring of protein electrophoresis in crosslinker-free linear polyacylamide solution," Electrophoresis 12:436–438 (1991).

Tietz, D., et al., "Electrophoresis on uncrosslinked polyacrylamide: Molecular Sieving and its potential applications," Electrophoresis 7:217–220 (1986).

Widhalm, A., and Schwer, C., "Capillary zone electrophoresis with a linear, non-cross-linked polyacrylamide gel: Separation of proteins according to molecular mass," J. Chromatographs 549:446–451 (1991).

Zhu, M., et al., "Factors Affecting Free Zone Electrophoresis and Isoelectric Focusing in Capillary Electrophoresis," J. Chromatogr. 480:311–319 (1989).

CAPILLARY ELECTROPHORESIS MOLECULAR WEIGHT SEPARATION OF BIOMOLECULES USING A POLYMER-CONTAINING SOLUTION

This application is a continuation-in-part of co-owned, co-pending U.S. application Ser. No. 07/682,582, filed 8 Apr. 1991, now U.S. Pat. No. 5,181,999, which is a continuation of U.S. application Ser. No. 07/432,061, filed 6 Nov. 1989, and issued on 14 May 1991 as U.S. Pat. No. 5,015,350.

FIELD OF THE INVENTION

The present invention relates to separation of biomolecules (such as polypeptides, nucleic acids, and oligosaccharides), and in particular, to the use of a low viscosity solution containing a hydrophilic polymer having a charge percent of between about 0.01 and 1.0% which is effective as both a molecular sieving matrix and a non-covalent wall coating for capillary electrophoresis.

REFERENCES

Alstine, J. M. V., et al., U.S. Pat. No. 4,690,749, issued Sep. 1, 1987.
Ausubel, F. M., et al., *Current Protocols in Molecular Biology*, John Wiley and Sons, Inc., Media Pa.
Bode, H.-J., Physiol. Chem. Bd. 359S:1237-1238 (1978).
Bohinski, R. C., *Modern Concepts in Biochemisty*, Second Edition, Allyn and Bacon, Inc.
Cantor, C. R., et al., P.C.T. International Application 83/US1826 111883, WO A1 840524 (1984).
Cantor, C. R., et al., Biochem. 27:9216-9221 (1988).
Cohen, A. S., et al., Anal Chem, 59:1021(1987).
Cohen, A. S., et al., J. Chromatography, 458:323 (1988).
Cohen, A., et al., U.S. Pat. No. 4,997,537, issued Mar. 5, 1991.
Compton, S. w., et al. BioTechniques, 6(5):432 (1988).
Jen, Yun, Canadian Patent No. 579(222), issued 7 Jul. 1959.
Karger, B. L., et al., European Patent Application No. EP 417925, issued Mar. 20, 1991.
Kaspar, T. J., et al., J Chromatography, 458:303 (1988).
Kulicke, W. M., et al., Prog Polym. Sci, 8:373 (1982).
Maniatis, T., et al. *Molecular Cloning: A Laboratory Manual*, Cold Spring Harbor Laboratory (1982).
Mathew, M. K., et al., Biochem. 27:9222-9226 (1988).
Mathew, M. K., et al., Biochem. 27:9204-9210 (1988).
Mathew, M. K., et al., Biochem. 27:9210-9216 (1988).
McKormic, C. L., et al., J. Macromol. Sci. Chem. A16(8):1441-1462 (1981).
Ogawa, M., U.S. Pat. No. 4,657,656, issued Apr. 14, 1987.
Ogawa, M., et al., U.S. Pat. No. 4,963,243, issued Oct. 16, 1990.
Takagi, T., et al., Electrophoresis, 12:436-438 (1991).
Widhalm, A., et al., Chromatographs 549:446-451 (1991).
Zhu, D-Z., et al., U.S. Pat. No. 5,069,766, issued Dec. 3, 1991.

BACKGROUND OF THE INVENTION

Electrophoresis is widely used for fractionation of a variety of biomolecules, including DNA species, proteins, peptides, and derivatized amino acids One electrophoretic technique which allows rapid, high-resolution separation is capillary electrophoresis (CE) (Cohen, 1987, 1988, Compton, Kaspar). Typically, the CE employs fused silica capillary tubes whose inner diameters are between about 10-200 microns, and which can range in length between about 5-100 cm or more.

In the usual electrophoresis procedure, an electrophoresis tube, or slab, is filled with a fluid electrophoresis medium, and the fluid medium is covalently cross-linked or temperature-solidified to form a non-flowable, stabilized gel separation medium. A sample volume is drawn into or added to one end of the tube, and an electric field is placed across the tube to draw the sample through the medium. Electrophoretic separation within the matrix may be based on molecular size, in the cases of denatured protein and nucleic acid species (which have roughly the same charge density), or on a combination of size and charge, in the case of peptides and proteins.

The polymer concentration and/or degree of cross-linking of the separation medium may be varied to provide separation of species over a wide range of molecular weights and charges. For separating nucleic acid fragments greater than about 1,000 bases, for example, one preferred temperature-solidified material is agarose, where the concentration of the agarose may vary from about 0.3%, for separating fragments in the 5-60 kilobase size range, up to about 2%, for separating fragments in the 100-3,000 basepair range (Maniatis). Smaller size fragments, typically less than about 1,000 basepairs, are usually separated in cross-linked polyacrylamide. The concentration of acrylamide polymer can range from about 3.5%, for separating fragments in the 100-1,000 basepair range, up to about 20%, for achieving separation in the size range 10-100 basepairs. For separating proteins, cross-linked polyacrylamide at concentrations between about 3%-20 percent are generally suitable. In general, the smaller the molecular species to be fractionated, the higher the concentration of cross-linked polymer.

The resolution obtainable in solidified electrophoresis media of the type described above has been limited, in the case of small molecular weight species, by difficulties in forming a homogeneous, uniform polymer matrix at high polymer concentration within an electrophoresis tube, and especially within a capillary tube. In the usual method for forming a high-concentration solidified matrix in a tube, a high-concentration monomer solution, (acrylamide and bisacrylamide), is introduced in fluid form fluid into the tube. The fluid material is then polymerized, for example, by exposure to light in the presence of persulfate.

At high polymer concentrations, reaction heat gradients formed within the tube tend to produce uneven rates of reaction and heat turbulence which can lead to matrix inhomogeneities. Also, entrapped gas bubbles generated during the cross-linking reaction produce voids throughout the matrix. The non-uniformities in the matrix limit the degree of resolution which can be achieved, particularly among closely related, small molecular weight species.

Alteratively, in the case of temperature-solidifying polymers the polymer is introduced into an electrophoresis tube in a fluid form, then allowed to gel to a solid form by cooling. This approach, however, is generally unsuitable for fractionating low molecular weight species, such as small peptides and oligonucleotides, since the polymers, such as agar and agarose, which are known to have the necessary temperature-solidifying setting properties are not effective for fractionating low molecular weight species, even at high polymer concentrations.

A second limitation associated with cross-linked or temperature solidified matrices is the difficulty in recovering fractionated molecular species within the matrix, after electrophoretic separation. In the case of a preparative-scale electrophoresis tube, the solidified matrix must be carefully separated from the walls of the tube before the matrix can be removed, a procedure which is virtually impossible with small diameter tubes. Even after the matrix is removed, and the region of the matrix containing the desired molecular species is identified, the species of interest can be recovered from the matrix region only by a lengthy elution procedure, or by electrophoretic elution.

In CE, coating materials have typically been covalently attached to the walls of microcapillary tubes (Cohen, et al., 1991; Karger, et al., 1989; Alstine, et al., 1987). Most commonly polymerized matrices are introduced after covalent attachment of the coating materials (Cohen, et al., 1991; Karger, et al., 1989). Water soluble polymers have been added to cross-linked, polymerized electrophoresis medium in order to reduce brittleness, i.e., improve ease of handling, and to improve migration velocity characteristics (Ogawa, 1987; Ogawa, et al., 1990).

Grossman (U.S. patent application Ser. No. 07/731,771, now allowed) described the use of an uncharged, water-soluble polymer in a low-viscosity solution which has a mesh size useful for capillary electrophoretic separation of biopolymers.

Wiktorowicz (U.S. Pat. No. 5,015,350) described the use of non-covalent coating to adjust electroosmotic flow for the separation of biomolecules. The capillary tube is connected between anodic and cathodic electrolyte reservoirs, and an electric field is placed across the reservoirs to produce electroosmotic flow within the tube. During electroosmotic flow, a compound capable of altering the surface charge of the tube is drawn into and through the tube, and the electroosmotic flow rate within the tube is monitored. The compound is continued to be drawn into and through the tube until a desired electroosmotic flow rate in the tube, as determined from said monitoring, is achieved.

Zhu, et al., (U.S. Pat. No. 5,069,766) described the suppression of electroosmotic flow during capillary electrophoresis by the inclusion of a viscosity raising additive in one or both of the electrode chamber solutions.

Size-fractionation of protein has been performed using liquid polyacrylamide (Widhalm, et al., 1991; Takagi, et al., 1991; Bode, 1978). However, protein separations using liquid polyacrylamide in CE has attendant problems involving (i) the effect of electroosmotic flow on protein or protein-complex migration (Widhalm, et al., 1991), (ii) the use of sufficiently high polyacrylamide concentrations to attain separation of sample proteins or protein-complexes into discrete bands (Takagi, et al., 1991), and (iii) trailing of protein bands (Bode, 1978).

SUMMARY OF THE INVENTION

The present invention provides a method of separating biomolecules in a sample. A capillary tube, having two ends, is prepared. The capillary tube
(i) has charged chemical groups on its inner wall surface, and
(ii) is filled with an electrolyte solution containing 0.05 to 30% weight to weight (w/w) of a non-cross-linked, hydrophilic polymer or copolymer solution containing at least one polymer or copolymer species having (a) a molecular weight between 20 and 5,000 kilodaltons, and (b) a percent charge of between 0.01 to 1.0%. The percent charge is measured by the molar percent of charged monomer subunits to the total polymer subunits, where the charged monomer subunits have the charge opposite to the wall charge at a selected electrophoresis pH. The ends of the tube are immersed in anodic and cathodic reservoirs containing an electrolyte solution. The sample, containing the biomolecules to be separated, is introduced into one end of the tube. An electrical field is then applied across the reservoirs with a polarity effective to fractionate said biomolecules in the sample.

Polymers or copolymers useful in the present invention include the following groups: polyacrylamides (such as, polyacrylamide and polymethacrylamide), polyoxides (such as, polyethyleneoxide and polypropylene oxide), polyethers (such as, polyvinylmethylether), vinyl polymers (such as, polyvinylpyrollydine, polyvinylalcohol, and polyvinylacetate), cellulose polymers (such as, methylcellulose, hydroxyethylcellulose, hydroxylpropylcellulose, and hydroxypropyl-methylcellulose), acrylic polymers (such as, polyhydroxyethylmethacrylate and polyethylene glycol monomethacrylate), natural gums and polysaccharides (such as, xanthans, dextrans, agar, guar, and starches).

The polymer or copolymer solution may contain a homopolymer, a copolymer, or a mixture of the two.

The polymer or copolymer molecules used in the practice of the present invention contain at least one charged group which has a charge selected from the group consisting of primary amines, secondary amines, quaternary amines, carboxylic acids, sulfonic acids, phosphoric acids, sulfuric acids, and phosphonic acids. The polymer or copolymer molecules may contain at least one charged group selected from the group consisting of primary amines, secondary amines, and quaternary amines, and at least one charged group selected from the group consisting of carboxylic acids, sulfonic acids, phosphoric acids, sulfuric acids, and phosphonic acids.

In one embodiment of the present invention the polymer is a copolymer of acrylamide and diallyldimethylammoniumchloride (DADMAC) and the copolymer has a molecular weight between about 200 and 600 kd. Further, the polymer molecules contain 0.05 to 0.5% of the quaternary amine N,N-dimethyl-3,5-methylene piperidine per subunit acrylamide.

In another embodiment of the present invention, the polymer is a copolymer of acrylamide and tetramethylethylenediamine (TEMED), and the copolymer has a molecular weight between about 100 and 500 kilodaltons. Further, the polymer molecules contain 0.02 to 0.4% of the tertiary amine tetramethylethylenediamine per subunit acrylamide.

In another embodiment, the concentration of polymer molecules containing a charge opposite the wall charge is sufficient to non-covalently coat the wall surface and significantly control and reduce electroosmotic flow to less than about $2 \times 10^{-5}$ cm$^2$/sec-V.

The method of the present invention may further include detecting the presence of separated biomolecules in the electrophoresis capillary tube by measuring electrochemical, optical (such as UV absorption or fluorescence) or radioisotopic properties of the biomolecules in the tube.

The present method can be applied to the separation of proteins, polypeptides, and peptides: these biomolecules may have a net positive or negative charge at the pH of the electrophoresis medium. In one embodiment, the biomolecules can be denatured before separation using, for example, sodium dodecylsulfate. The denaturant, for example sodium dodecylsulfate, may also be present in the electrolyte solution.

Further, the present method can be applied to the separation of nucleic acid fragments. The nucleic acid fragments can be DNA or RNA, single- or double-stranded. The differential migration of double-stranded nucleic acids can be adjusted by the addition of an intercalating agent to the fragments, to increase preferentially the migration rates of smaller molecular weight fragments through the polymer solution. Examples of such intercalating agents are ethidium bromide and acridine orange. The method of the present invention can be applied to performing restriction digest analysis of a DNA sample—after the sample has been treated with one or more selected restriction endonucleases.

The method of the present invention can also be applied to the separation of linear, branched, native and chemically modified oligosaccharides.

The present invention further comprises a filled capillary tube for use in the method of the present invention. The capillary tube has charged chemical groups on its inner wall surface, and is filled with an electrolyte solution containing 0.05 to 30% weight to weight (w/w) of a non-cross-linked, hydrophilic polymer or copolymer solution containing at least one polymer or copolymer species having (a) a molecular weight between 20 and 5,000 kilodaltons, and (b) a percent charge of between 0.01 to 1.0%. As above, the percent charge is measured by the molar percent of charged monomer subunits to the total polymer subunits, where the charged monomer subunits have the charge opposite to the wall charge at a selected electrophoresis pH.

The polymers and charged groups described above may be used to fill the capillary tube.

DEFINITIONS OF TERMS

Figure 8:
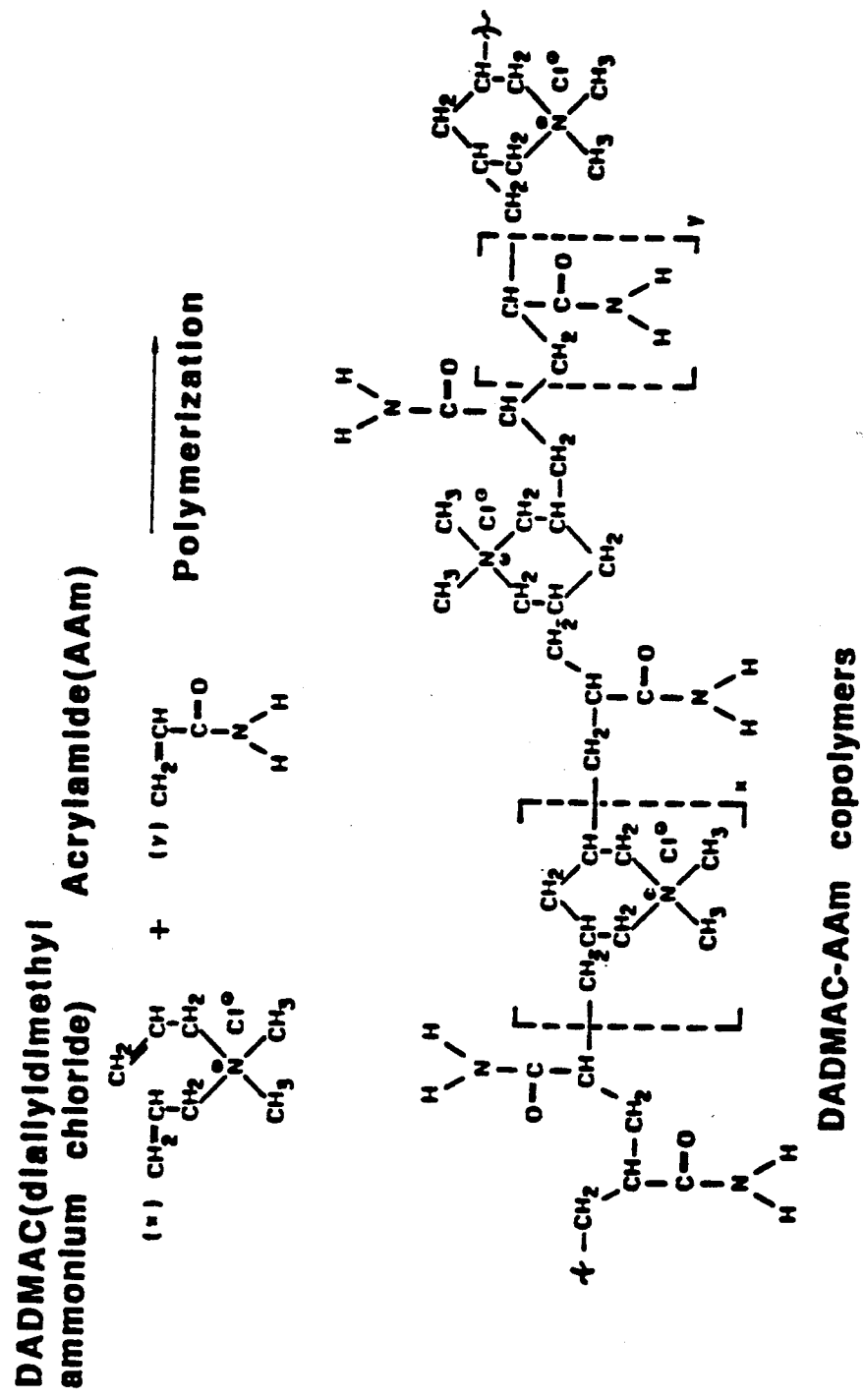
FIG. 8 shows a proposed structure for a linear copolymer made from the acrylamide and DADMAC subunits.

The term polymer in the present invention is used in its traditional sense of a large molecule composed of smaller monomeric subunits covalently linked together in a characteristic fashion: i.e., a homopolymer made of up identical subunits. The term copolymer is used to refer a polymer that contains two or more kinds of monomeric units in the same molecule. Through copolymerization there can be made copolymer materials with different properties than those of either homopolymer. An example of a copolymer in the present invention is a mixture of acrylamide and DADMAC to form linear polymer having the proposed structure shown in FIG. 8. In the specification, a polymer solution refers to a solution containing a polymer, mixture of polymers, copolymer, mixture of copolymers, or mixture of polymers and copolymers.

The term hydrophilic describes a polymer/copolymer which is soluble in water or water buffer systems.

In the context of the present invention the term biomolecules typically refers to proteins, polypeptides, peptides, nucleic acids, single and double stranded DNA and/or RNA. Other biomolecules such as oligosaccharides or glycoproteins may also be analyzed by the method of the present invention. Biomolecules may be linear, branched, native or chemically modified.

Proteins are typically long chains of amino acid based polymers (polypeptides). Proteins may be composed of one, two or more polypeptide chains and may further contain some other type of substance in association with the polypeptide chain(s), such as iron or carbohydrates. The size of proteins covers a rather wide range from (an arbitrary figure of) 5,000 to several hundred thousand g/mole. The 5,000 figure corresponds to the presence or roughly 40-45 amino acids. Proteins smaller than about 5,000 g/mole are typically referred to as polypeptides or simply peptides (Bohinski).

Percent charge for polymers and/or copolymers in an electrolyte solution is measured as the molar percent of charged monomer subunits relative to the total polymer subunits.

DETAILED DESCRIPTION OF THE INVENTION

The present invention describes the use of at least one polymer or copolymer in an electrolyte solution for use in the separation of biomolecules. The polymer containing electrolyte solution (polymer solution) of the present invention is typically introduced into a capillary tube, where the capillary tube has charged chemical groups on its inner wall surface: exemplary of capillaries with negatively charged groups on the inner surface wall are glass or fused silica. The capillary tube is then filled with a polymer solution containing 0.05 to 30% weight to weight (w/w) of a non-cross-linked, hydrophilic polymer or copolymer: the solution may contain one or more polymer or copolymer species. Typically, the polymer or copolymer species has (i) a molecular weight between 20 and 5,000 kilodaltons and (ii) a percent charge of between 0.01 to 1.0%. At a selected electrophoresis pH, a charge on the polymer or copolymer is opposite to the charged chemical groups on the inner wall surface of the capillary tube.

The ends of the capillary tube are immersed in anodic and cathodic reservoirs which contain the above-described polymer containing electrolyte solution. Samples of biomolecules or biomolecule mixtures are introduced into one end of the capillary tube and an electric field is applied across the reservoirs. As the charged biomolecules move through the electric field, they are fractionated on the basis of size and/or shape by differential migration through the sieving matrix established by the polymer solution.

I. Capillary Electrophoresis System

Figure 1:
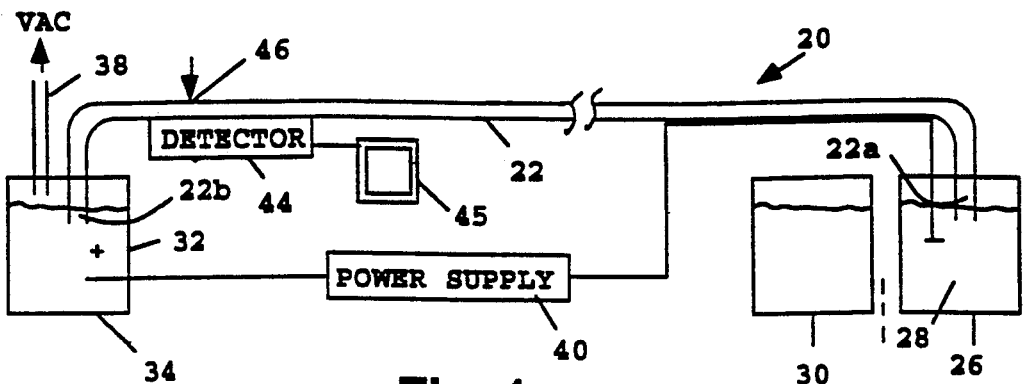
FIG. 1 is a simplified schematic view of a capillary electrophoresis system used in practicing the method of the invention.

FIG. 1 is a simplified schematic view of a capillary electrophoresis system 20 (Applied Biosystems, Foster City Calif.) suitable for practicing the method of the invention. The system includes a capillary tube 22 having a length preferably between about 10-200 cm, typically less than about 100 cm, and an inner diameter of preferably between about 10-200 $\mu$m (microns), typically about 50 $\mu$m. In the embodiment shown, the tube is supported in a horizontal position and has downwardly bent end regions. One preferred capillary tube is a fused silica tube having an inner diameter of 50 $\mu$m and available from Polymicro Technologies (Phoenix, Ariz.).

More generally, the capillary tube may be any tube or channel capable of supporting a column of polymer solution, preferably at a column internal or diameter thickness of 200 $\mu$m or less. For example, the tube may take the form of a channel formed in a glass slide or the like.

The inner surface of the capillary tube typically has charged chemical groups on its inner wall surface. In one embodiment of the present invention, the inner surface of the tube has negatively charged chemical groups at the pH preferably between about 4-9. The surface chemical groups may be an inherent property of the capillary material, such as is the case for a fused silica tube which has surface negatively charged silanol groups. Alternatively, or in addition, the capillary walls may be treated with known derivatization reagents for covalent attachment of negative chemical groups, such as acid groups, to the inner capillary walls, or with known negatively charged surface-coating agents. Alternatively, the inner wall surface may be covalently modified to have positively charged groups covalently attached to the inner wall surface. Methods for derivatizing or coating glass or the like are well known in the art. One preferred capillary tube is a fused silica tube having an inner diameter of 50 $\mu$m and available from Polymicro Technologies (Phoenix, Ariz.).

The polarities indicated below may be switched depending on the biomolecules to be separated: the detector side reservoir and the sample side reservoir—cathodic to anodic or anodic to cathodic. The polarities of the run, relative to the charge in each reservoir, can be chosen on many capillary electrophoresis machines.

A cathodic reservoir 26 in the system contains an electrolytic polymer solution 28; the polymer solution is described below. The cathodic end of the tube, indicated at 22a, is immersed in the polymer solution, as shown, during electrophoresis.

A sample tube 30 in the system contains the biomolecule mixture which is to be loaded into the cathodic end of the tube. Preferably the sample material is dissolved in dilute electrolytic solution or in water. The sample and cathodic reservoirs may be carried on a carousel or the like, for placement at a position in which the lower cathodic end of the tube can be immersed in the reservoir fluid. Although not shown here, the carousel may carry additional reservoirs containing, for example, solutions for cleaning and flushing the tube between electrophoretic runs or different polymer solutions.

The opposite, anodic end of the tube, indicated at 22b, is sealed within an anodic reservoir 32 and is immersed in an anodic polymer containing electrolyte solution 34 contained in the reservoir, as shown. The second tube 38 in the reservoir is connected to a finely-controlled vacuum system (not shown) for drawing fluid, e.g., washing and cleaning solutions, electrophoresis polymer solution, through the tube and for loading the biomolecule sample material in reservoir 30 into the tube. As an alternative to the vacuum system a positive pressure system can be used to introduce cleaning solutions, samples, etc.

A high voltage supply 40 in the system is connected to the cathodic and anodic reservoirs as shown, for applying a selected electric potential between the two reservoirs. The power supply leads are connected to platinum electrodes 41, 42 in the cathodic and anodic reservoirs, respectively. The power supply may be designed for applying a constant voltage (DC) across the electrodes, preferably at a voltage setting of between 5-50 KV. Alternatively, or in addition, the power supply may be designed to apply a selected-frequency, pulsed voltage between the reservoirs. In general, the shorter the capillary tube, the higher the electric field strength that can be applied, and the more rapid the electrophoretic separation. When operated in a pulsed voltage mode, the power supply preferably outputs a square wave pulse at an adjustable frequency of about 50 Hz up to a KHz range, and an rms voltage output of about 10-30 KV. Higher pulse frequencies, even into the MHz range may be suitable for some applications.

Completing the description of the system shown in FIG. 1, a detector 44 in the system is positioned adjacent the anodic end of the tube, for optically (such as UV absorbance or fluorescnce) monitoring biomolecules migrating through an optical detection zone 46 in the tube. The detector may be designed either for UV or visible absorption detection and/or for fluorescence emission detection or radioisotope detection. UV absorbance is typically carried out at 200–280 range nm, using, for example, a built-in UV absorbance detector in the Applied Biosystem Model 270 Capillary Electrophoresis system, which has a flow cell with a capillary holder.

Fluorescence emission detection is preferably carried out at a selected excitation wavelength which is adjustable between about 240–500 nm, depending on the fluorescent species associated with the biomolecule, as discussed below. One exemplary fluorescence detector is an HP1046A detector available from Hewlett-Packard (Palo Alto, Calif.), and modified as above for capillary tube detection. The detector is connected to an integrator/plotter 45 for recording electrophoretic peaks.

Radioisotope detection may be accomplished by the use of a modified HPLC isotope detector for $^3H$ or $^{14}C$ (Radiomatic Instruments & Chemical Co., Inc., Meriden, Conn.).

In operation, the capillary tube is thoroughly washed by drawing suitable cleaning and rinsing solutions through the tube by applying a vacuum to reservoir 32, such as detailed in Example 2. In the practice of the present invention the polymer-containing electrolyte solution itself can be used to flush the system between sample runs. If a cleaning solution different than the polymer-containing electrolyte solution is used, the tube is then flushed with several volumes of the electrolytic polymer solution. A small volume, typically 1–10 nanoliters of sample material is loaded into the cathodic tube end by vacuum injection. A voltage is applied between the cathodic and anodic reservoirs until all of the biomolecule peaks have passed through the detection zone.

Figure 2:
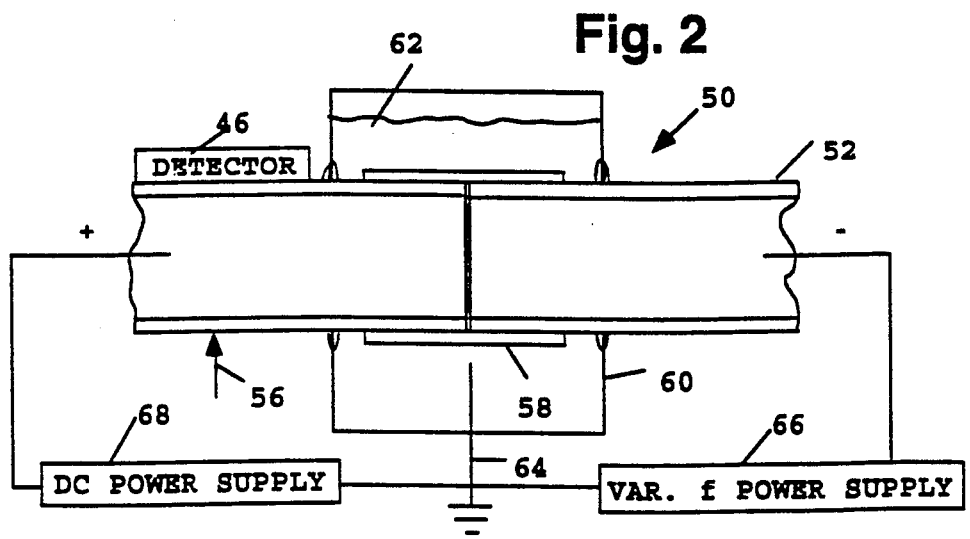
FIG. 2 is a schematic view of a capillary electrophoresis system designed for operation simultaneously in both a pulsed and constant-voltage mode.

FIG. 2 shows a fragmentary view of an electrophoretic system 50 which can be operated to the end of the electrophoretic run under a pulsed field. The capillary tube 52 in the system has a small-clearance break 54 adjacent and upstream of the detection zone, indicated at 56. The tube sections on either side of the break are coupled by porous glass sleeve 58 which allows electrolyte migration into and out of the tube. The coupled portion of the tube is sealed within a reservoir 60 filled with a suitable polymer-containing electrolyte solution 62. A grounded electrode 64 in the reservoir is connected to the high-voltage side of a pulsed-voltage power supply 66 whose negative side is in communication with a suitable cathodic reservoir. The grounded electrode is 64 is connected to the high-voltage side of a DC power supply 68 whose negative side is in communication with a suitable anodic reservoir.

In operation, after sample material is loaded into the cathodic end of the tube, the pulsed-voltage power supply is adjusted to a desired voltage and frequency level, and the DC power supply to a desired voltage level. Biomolecules in the sample are fractionated under the pulsed field within the portion upstream of break 54. Thereafter, the fragments are carried in a constant-voltage field through the detection zone, where the fragments can be optically detected without pulse-frequency noise effects.

Although not shown here, it will also be appreciated that the electrophoresis system can be readily adapted for collecting separated biomolecules for preparative electrophoresis applications. Sample collection may be accomplished, for example, by providing a series of cathodic reservoirs into which the fragments can be eluted.

II. Viscosity Characteristics

Viscosity of the polymer or copolymer solution is a factor in the present invention which determines the rate at which the solution can be pulled or pushed through a capillary using the pressures found on conventional capillary electrophoresis instruments. The rate of solution flow through the capillary determines how much time is required to replace the solution matrix between sequential analyses. An excessive replacement time makes the current invention less practical or convenient. The flow rate, v, of a fluid with a viscosity, $\eta$, moving through a capillary tube of length, L, and radius, r, and pressure, p, between the ends is expressed by the Poiseuille equation:

$$v = \pi p r^4 / 8 L \eta$$

This equation can be rearranged to calculate viscosity of a solution that would take time, t, to replace the entire volume in the capillary tube as:

$$\eta = t p r^2 / 8 L^2$$

For example, a capillary that is 50 cm long (L=50), with a diameter of 50 μM (r=0.0025 cm), subjected to a pressure of 20″ Hg (p=0.678 Bar), would require a solution viscosity of less than 38 centipoise ($\eta$=0.38 poise) to have its volume replaced in less than 30 minutes (t=1800 seconds), a time which would be considered excessive for conventional capillary electrophoresis.

The viscosity of the polymer/copolymer solution is determined in the present invention by the molecular weight of the polymer and its concentration in the solution. The specific viscosity, $\eta_{sp}$, of the solutions is calculated by measuring the time, t, for the polymer solution, and time, $t_0$, for water to flow through a capillary tube at a constant, regulated pressure and temperature. The ABI Model 270 Capillary Electrophoresis is used as the capillary viscometer in this case with a pressure of 20″ Hg and temperature of 30° C. The specific viscosity is calculated thus:

$$\eta_{sp} = (t/to) - 1$$

Figure 13:
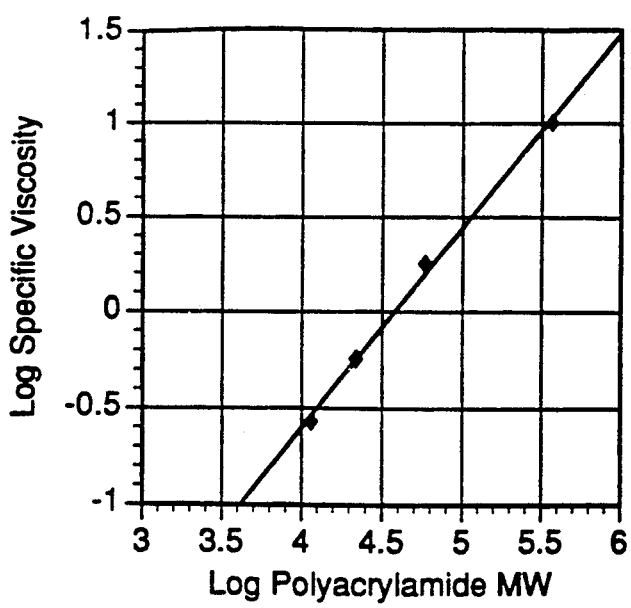
FIG. 13 shows a plot of the log Specific Viscosity versus the log of Polyacrylamide molecular weight standards.

By using a 2% solution of standard MW linear polyacrylamides (polyacrylamide, formed by linear polymerization of acrylamide molecules, is available in a wide range of molecular weights; Polysciences, Inc., Warrington, Pa.), a good linear correlation is shown in FIG. 13 between the log of the specific viscosity (measured as described above) and the log of the molecular weight. The slope of this correlation is 1.042 and, in agreement with conventional techniques, this viscosity is a direct measure of the size of the polymer/copolymer in solution. Thus, using our example of a viscosity of less than 38 centipoise (specific viscosity of 30), a 2% polymer solution should use a polyacrylamide of MW less than about 790,000 to avoid excessive replacement times.

Figure 14:
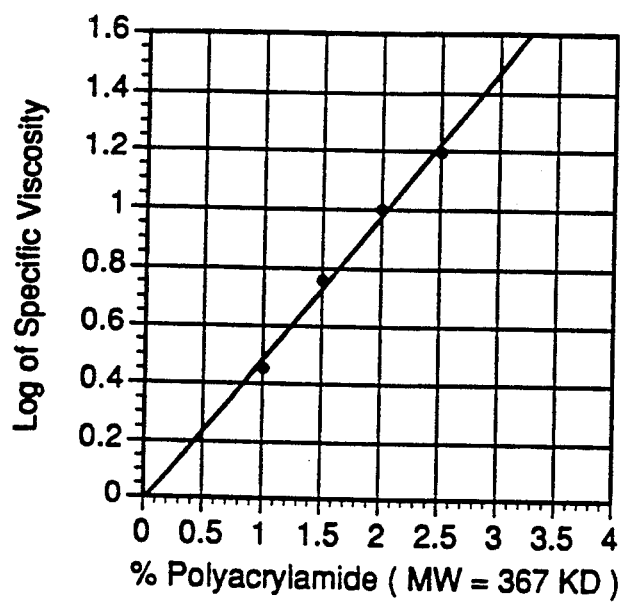
FIG. 14 shows a plot of the log Specific Viscosity versus the percent concentration of a single-molecular weight polyacrylamide (367 kD).

When the concentration of the polymer or copolymer is increased in the solution, there is a corresponding increase in the viscosity of the solution. This fact is shown in FIG. 14 where there is a good linear correlation between the log of the specific viscosity and the % (w/v) of a 367,000 Dalton MW linear polyacrylamide (Polysciences, Inc.) in solution. So, in the example of a specific viscosity of less than 30, a 367 KD polyacrylamide should be present in solution at less than about 3.1% (w/v) to avoid excess replacement times.

The relationship between viscosity and concentration of the polymer/copolymer suggests that if high concentration is required to obtain resolution of biomolecules in a mixture, then a lower molecular weight polymer/copolymer can be used to keep the viscosity low. Conversely, at lower percent concentrations of polymer/copolymer higher molecular weight polymer/copolymers can be used.

The MW of the polymer or copolymer is adjusted by a number of different methods. First, the conditions of polymerization are changed in order to effect changes in the MW of the final polymer product. The viscosity average MW of the copolymer/polymer is decreased by (1) increasing the reaction temperature, (2) increasing the content of a water miscible solvent in the reaction mixture, such as methanol, or (3) increasing initiator concentrations. The data in FIG. 4 demonstrates that as the initial concentration of the redox initiator, TEMED, is increased, the viscosity, and MW, of the polyacrylamide copolymer decreased. The above list of reaction conditions is not inclusive, as other polymerization conditions or additives are used to control MW, dependent on the particular polymer/copolymer that is made.

A second method of adjusting the average MW of a polymer/copolymer is by fractionating a polydisperse polymer product into different MW fractions followed by isolation and purification. An aqueous solution of polymer/copolymer is fractionated by (1) a size-dependent chromatographic separation (such as gel permeation chromatography), (2) a dialysis using membranes of specified MW cut-offs, or (3) fractional precipitations using a water miscible solvent such as methanol.

The concentration of the polymer/copolymer solution is adjusted by (1) adding different weights of solid polymer to a specified volume of aqueous buffer and mixing until the solid is completely dissolved or (2) adding different weights or volumes of a concentrated aqueous polymer solution to a specified volume of aqueous buffer and mixing until the concentrate is completely dispersed.

It is clear that the upper limits of polymer/copolymer MW and/or its concentration in solution will be dictated by primarily the upper viscosity that can be pushed or pulled through a capillary. This upper viscosity is set by the instrumental parameters as expressed in the previous equations. Thus, for example, if the capillary electrophoresis used a short capillary (L=20 cm) with a large radius (r=0.01 cm), a solution with a viscosity of about 38625 centipoise could be pushed through the capillary in 30 minutes at high pressure (P=100 psi=6.87 bar). Using the data of FIG. 13 (log Specific Viscosity vs. Polyacrylamide concentration), it can be estimated that the upper concentration is about 9% (w/v) for a polyacrylamide of MW=367 KD. Obviously, by utilizing a polyacrylamide of lower MW, solutions for higher concentrations could be pushed through a capillary and it is not unreasonable to expect that concentrations approaching 20% (w/v) would be useable.

As is clear from the relationships set forth above, an instrument that has higher pressure can give a higher flow rate for a given concentration of polymer relative to an instrument which generates a lower pressure. As a further example, a larger diameter capillary can give a higher flow rate relative to a smaller diameter capillary tube. The factors affecting flow rate can be manipulated based on the parameters defined above which affect flow rate.

III. Polymer Solutions and Electroosmotic Flow

Figure 3:
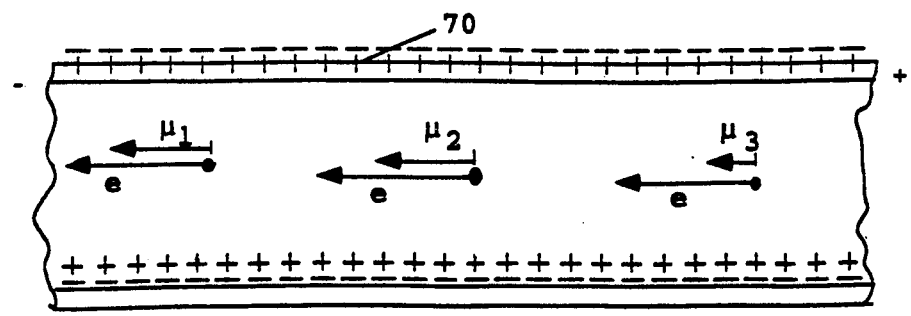
FIG. 3 is an enlarged, fragmentary portion of a capillary electrophoresis tube, illustrating electroosmotic flow (e) in a right-to-left direction.

The phenomenon of electroosmotic flow in a polymer solution matrix is described for an inner capillary tube wall having net negative charge with reference to FIG. 3, which shows an enlarged, fragmentary portion of a capillary electrophoresis tube 70.

As seen in FIG. 3, the negatively charged groups on the inner tube wall, indicated by "−" symbols, are shielded by both loosely and tightly bound positively charged ions present in the polymer electrolyte solution, essentially forming a positively charged shell about the column of fluid in the tube. The thickness of the shell of positive ions at the wall surface is known as the electrical double layer. The electric double layer is characterized by a zeta potential, which is a measure of the potential at the capillary wall.

Under the influence of an electric field, this column of polymer solution in the medium (which is surrounded by a shell of positive charges) is drawn electroosmotically in the direction of movement of the positive shell, (i.e., towards the cathode). The rate of electroosmotic flow in the tube is indicated by the arrow e in the figure (arrow e may be thought of as a vector with a magnitude e and a direction along the axis of the tube). The electroosmotic flow rate e in a capillary tube can be described by the equation:

$$e = \epsilon \zeta E / 4\pi \eta$$

where $\epsilon$, $\eta$, $\zeta$, and E are the dielectric constant of the double layer, its viscosity; the zeta potential; and the electrical field strength, respectively.

In the method of the present invention, the polymers or copolymers in the electrolyte solution have a sufficient percent charge to bind to the oppositely charged capillary wall. This binding significantly reduces or eliminates electroosmotic flow in the capillary tube by decreasing the dielectric constant, or increasing the viscosity, or both, of the electrical double layer. The level of electroosmotic flow must be reduced sufficiently to allow for discrete peaks or bands of separated biomolecules without substantial tailing, or broadening, of the bands, i.e., decreased resolution. As mentioned above, separation of biomolecules by the method of the present invention, relies predominantly on the sieving effect provided by the polymers and/or copolymers in the electrolyte solution. The effect of the percent charge in a particular polymer/copolymer solution on electroosmotic flow can be evaluated as follows.

Electroosmotic flow is typically measured as the mobility ($cm^2$:/sec-V) of an electrically neutral substance through a capillary tube containing a defined polymer/copolymer electrolyte solution (Example 2).

IV. Separation of Biomolecules

The separation method of the present invention can employ a number of polymers and copolymers in formulation of the polymer-containing electrolyte solution.

Typically, the polymers or copolymers used in the method of the present invention have a molecular weight of between 20 and 5,000 kilodaltons. Exemplary polymers and copolymers useful in the present method including the following: polyacrylamides, such as polyacrylamide and polymethacrylamide; polyoxides, such as polyethyleneoxide and polypropylene oxide; polyethers, such as polyvinylmethylether; vinyl polymers, such as polyvinylpyrollydine, polyvinylalcohol, and polyvinylacetate; natural gums or polysaccharides, such as xanthans, dextrans, agar, guar and starches; cellulose polymers, such as methylcellulose, hydroxyethylcellulose, hydroxylpropylcellulose, and hydroxypropylmethylcellulose; and acrylic polymers, such as polyhydroxyethylmethacrylate and polyethylene glycol monomethacrylate. Mixtures of polymers and copolymers can also be used in the practice of the present invention.

The percent charge of a selected polymer or copolymer can be achieved in a number of ways (Example 1). When homopolymers are used in the method of the present invention they can be modified to contain a specified percent charge. After or during polymerization, a homopolymer may be modified to contain a desired average percent charge, such as applying a Hoffman degradation to polyacrylamide to produce vinylamines (Kulicke). An example of a homopolymer is polyacrylamide, available in a wide range of molecular weights, linearly polymerized in the presence of ammonium persulfate to form a polyacrylamide molecule.

Copolymers are also useful in the method of the present invention. One advantage of copolymers is that one of the subunits may be specifically chosen to contain a desired charge group. This subunit can then be added to polymerization reactions with another subunit at a defined concentration thereby allowing formation of a copolymer having the desired percent charge characteristics. For example, copolymers of acrylamide ($[AA_m]$) and tetramethylethylenediamine (TEMED), or acrylamide and diallyldimethylammoniumchloride (DADMAC) can be formed as described in Example 1. These copolymers can cover a wide range of percent charge values, as well as a range of viscosity values.

Further, graft or block copolymers are also useful in the practice of the present invention. Aqueous graft charged polymers can be formed by polymerization of charged copolymers in the presence of uncharged polymers. One example of such a grafting reaction is presented in Example 1D for the grafting copolymer of acrylamide and DADMAC onto dextran.

Charged groups or subunits useful in modification of the polymers and copolymers of the present invention include the following: primary amines, such as vinylamine, glucosamine; secondary amines, such as ethylenimine; tertiary amines, such as vinyl pyridine, and tetramethylethylenediamine (TEMED); quaternary amines, such as vinyl-N-methylpyridine, N,N-dimethyl-3,5-methylene piperidine (DADMAC); carboxylic acids, such as acrylic acid, methacrylic acid, and malic acid; sulfonic acids, such as vinyl sulfonic acid; phosphoric acids, such as vinyl phosphoric; sulfuric acids, such as vinyl sulfuric; and phosphonic acids, such as vinylphosphonic.

The above-listed molecules containing charged groups can be incorporated in homopolymers by methods known in the art (see Example 1). Polymers and copolymers useful in the present invention may also be ampholytic polymers which contain both positive and negative charge groups: the different charged units can be introduced into the same polymer, including mixes of positive and negative charge groups. For example, the polymer or copolymer molecules may contain at least primary amine, secondary amine, and/or quaternary amine group, and at least carboxylic acid, sulfonic acid, phosphoric acid, sulfuric acid, and/or phosphonic acid group. Use of such ampholytic polymers may be useful for separations since, for example, the positive charge on the polymer can bond non-covalently with the negative capillary wall, and the slight negative charge on the polymer may improve separation by charge repulsion. In solution, the positive and negative charges on the polymer may also bond non-covalently and modify the sieving properties of the matrix.

In several cases, the above-listed charge group-containing molecules can also be directly incorporated into co-polymers as, for example, is illustrated in Example 1 for acrylamide and DADMAC.

Example 2 describes the use of copolymers of acrylamide ($[AA_m]$) and TEMED or DADMAC. The rate of electroosmotic flow was measured using a neutral marker. The proportions of TEMED or DADMAC to $[AA_m]$ were varied over the ranges of values shown at the bottom of FIGS. 4 and 5. In the cases of both TEMED and DADMAC, the rate of electroosmotic flow (EOF) was significantly reduced (less than about $2 \times 10^{-5}$ cm$^2$/sec-V) at percent charge values of 0.05%.

Figure 4:
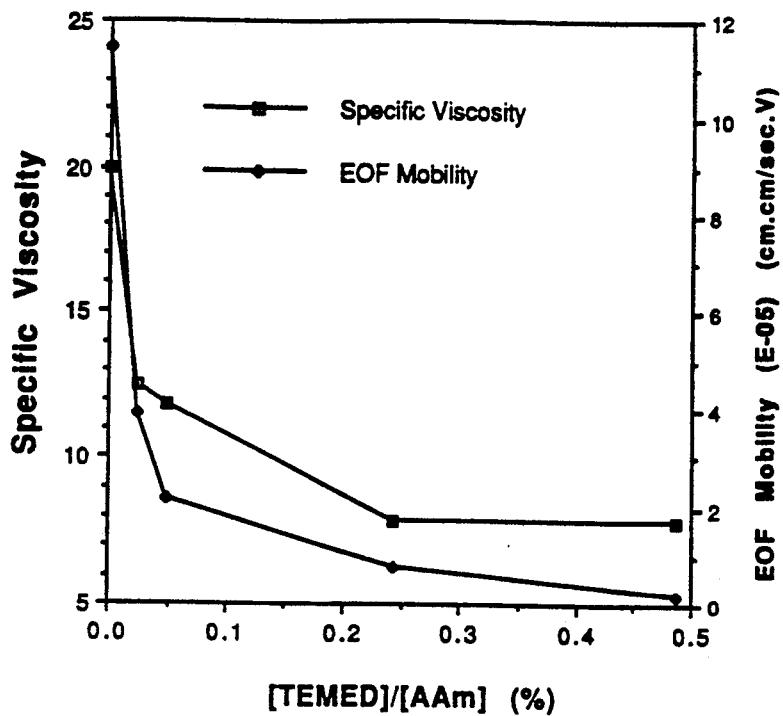
FIG. 4 shows the effects on viscosity and EOF of 2% (w/v) poly-acrylamide by increasing TEMED concentration in polymerization reactions.

FIG. 4 shows the effects on viscosity and EOF of increasing TEMED concentration in polymerization reactions. Using a constant polyacrylamide concentration of 2% (w/w) to measure EOF, the EOF decreased with increasing % TEMED and the results presented in FIG. 4 show that the EOF remains below $2 \times 10^{-5}$ cm$^2$/sec-V for percent charge values covering the range of approximately 0.05% to 0.5%. The viscosity of the polymer solution decreased with increasing % TEMED and remained relatively constant above about 0.2%. These data demonstrate that increases in the percent positive charge and not increases in viscosity, result in a decrease in EOF.

Figure 5:
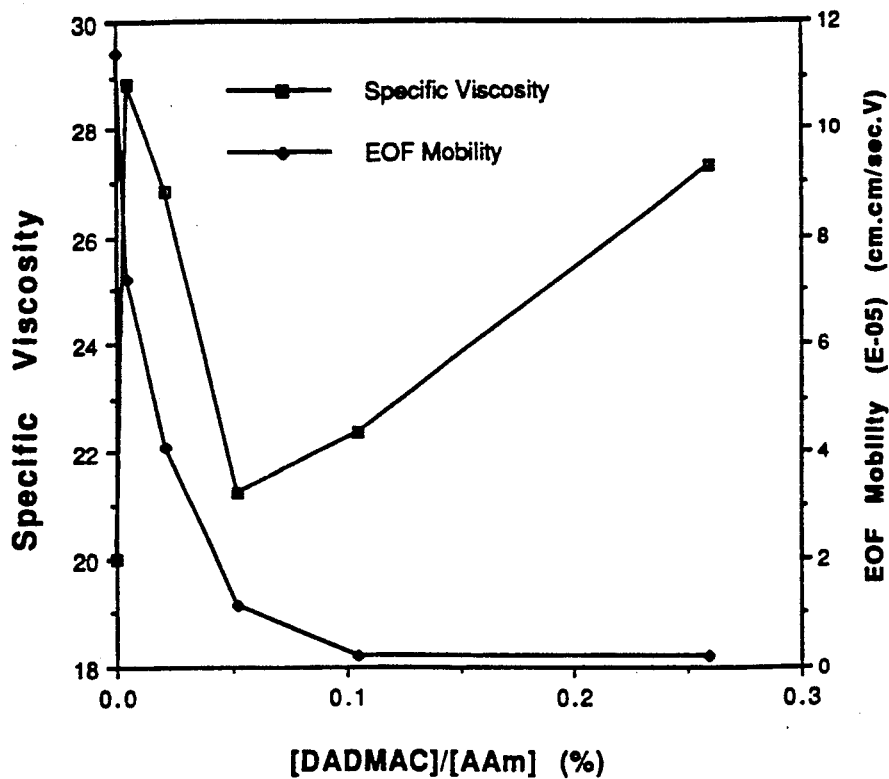
FIG. 5 shows the effects on viscosity and EOF of 2% (w/v) poly-acrylamide by increasing DADMAC concentration in polymerization reactions.

FIG. 5 shows the effects on viscosity and EOF of 2% (w/w) polyacrylamide made with increasing DADMAC concentration in polymerization reactions. As can be seen from the results presented in FIG. 5, EOF decreases with increasing % DADMAC and remains below $2 \times 10^{-5}$ cm$^2$/sec-V for percent charge values covering the range of approximately 0.05% to 0.26%. The viscosity of the polymer solution increases and decreases with increasing DADMAC but increases in a linear fashion in the same range of 0.05 to 0.26%. DADMAC/$[AA_m]$ copolymers having percent charge values in the range of 0.05% to 0.5% are useful for the separation of a wide variety of biomolecules having different size and/or shape. Thus, this data also shows that the decrease in EOF is due to increasing % of positive charge and not due to increasing viscosity.

The procedure described in Example 2 is useful for the control of percent charge, contained in polymers or copolymers to be used in the practice of the method of the present invention, in order to obtain a reduced EOF.

For the separation of biomolecules the capillary tube is typically filled with an electrolyte solution containing 0.05 to 30% weight to weight (w/w) of a non-crosslinked, hydrophilic polymer or copolymer solution which contains at least one polymer or copolymer species having (a) a molecular weight between 20 and 5,000 kilodaltons, and (b) a percent charge of between 0.01 to 1.0% as measured by the molar percent of charged monomer subunits to the total polymer subunits. A charge on the polymer or copolymer in solution is opposite to the wall charge at a selected electrophoresis pH.

The results presented in FIGS. 4 and 5 demonstrate that it is not viscosity that is responsible for the reduction of EOF, rather it is the percent charge of the polymer/copolymer molecule.

Figure 6:
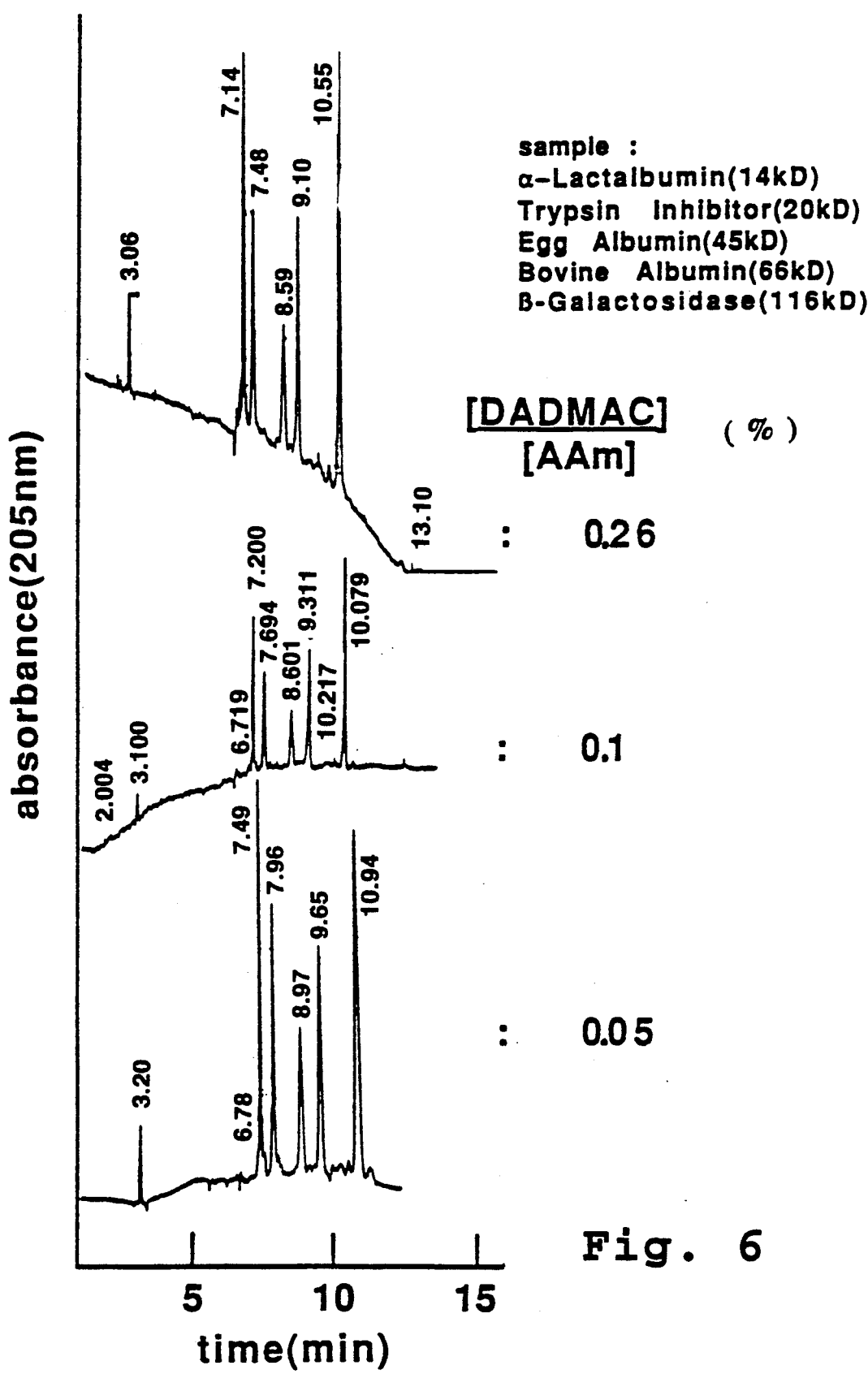
FIG. 6 shows the separation into discrete peaks of a protein mixture having multiple components. The copolymer DADMAC/[AA$_m$] % used for the separation is shown to the right of each electropherogram.

Example 3 describes the use of a number of copolymer solutions for the separation of biomolecules. The separation of a mixture of proteins was used to illustrate the molecular sieving capabilities of the present method. FIG. 6 shows the separation into discrete peaks of a protein mixture having the following components: $\alpha$-lactalbumin (14 kd), trypsin inhibitor (20 kd), egg albumin (45 kd), bovine albumin (66 kd), and $\beta$-galactosidase (116 kd). In FIG. 6 the order of the peaks from left to right corresponds, respectively, to the just-listed proteins. The DADMAC/[AA$_m$] % used for the separation is shown to the right of each electropherogram. As can be seen from FIG. 6, percent charge values in the range of 0.26, 0.1, to 0.05% are all effective for the separation of each protein in the protein mixture. Comparison of the separation ability of the copolymer electrolyte solution (FIG. 6) to the EOF of the same copolymer solution (FIG. 5) shows that each of the values 0.26, 0.1, and 0.05% have an EOF mobility value of less than $2 \times 10^{-5}$ cm$^2$/sec-V.

At the 0.26% value, significant baseline, downward sloping occurs which would obscure data at the longer run times. In general, the upper limit of percent charge is determined as that value which does not cause significant baseline pertubations (i.e., sloping, spiking, etc.). Although it is dependent on the polymer type, this upper value rarely exceeds 1%.

Figure 7:
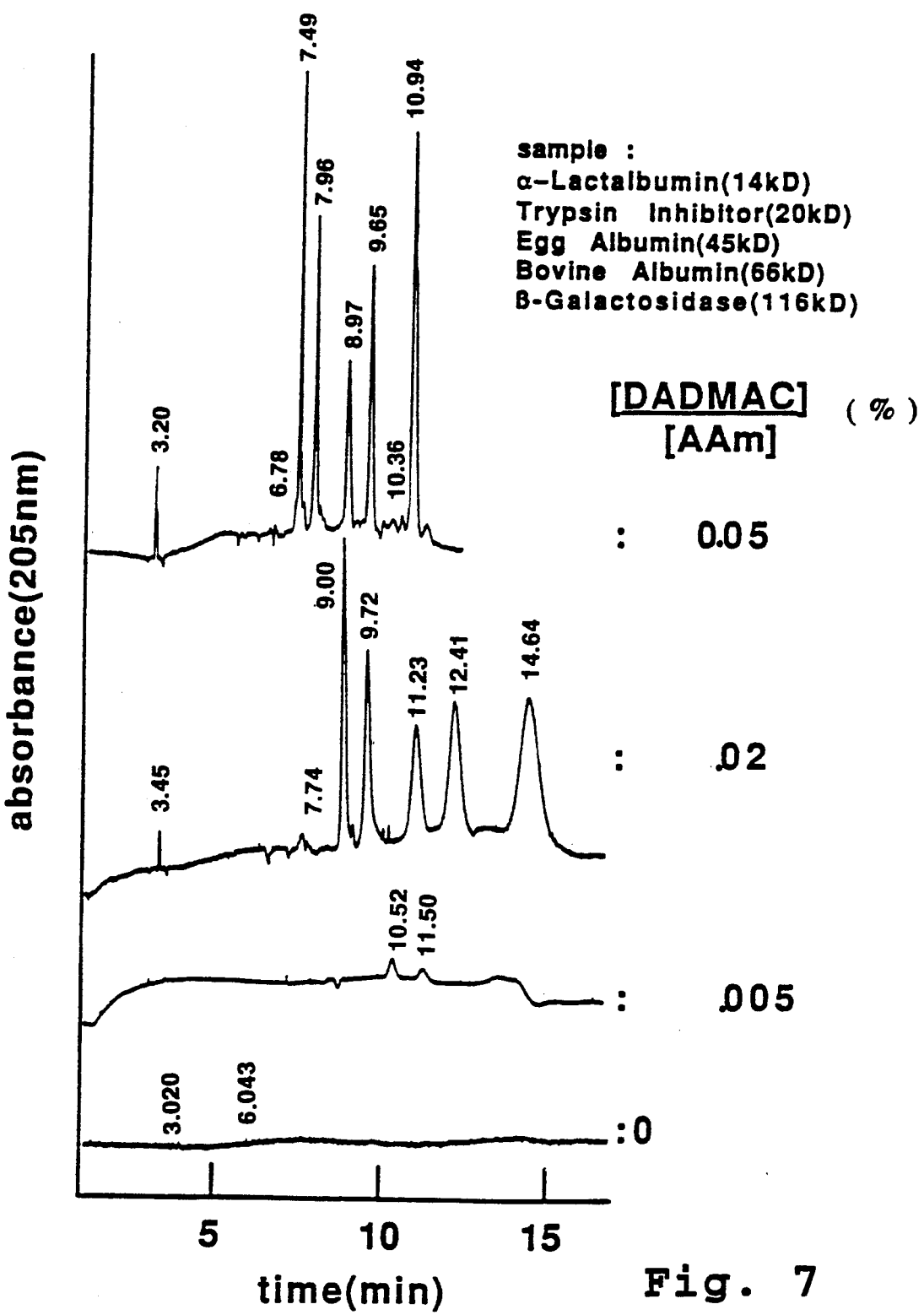
FIG. 7 shows the separation into discrete peaks of the above-described protein mixture. The copolymer DADMAC/[AA$_m$] % used for the separation is shown to the right of each electropherogram.

FIG. 7 shows the separation into discrete peaks of the above-described protein mixture. The DADMAC/[AA$_m$] % used for the separation is shown to the right of each electropherogram. As can be seen from FIG. 7, percent charge values of 0.02% and less are ineffective for the separation of each protein in the protein mixture because of significant band-broadening and loss of sensitivity. Comparison of the separation ability of the copolymer electrolyte solution (FIG. 7) to the EOF of the same copolymer solution (FIG. 5) shows that each of the values 0.02% and less have an EOF mobility value of greater than $2 \times 10^{-5}$ cm$^2$/sec-V.

Figure 10:
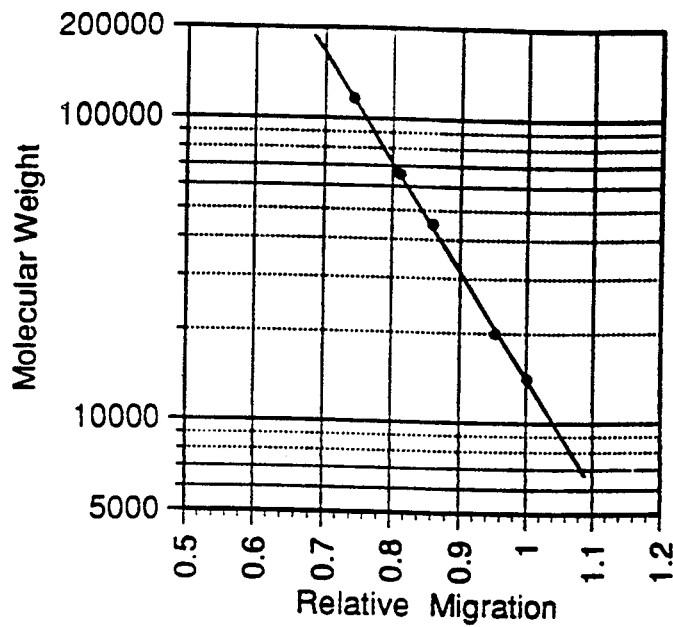
FIG. 10 shows the results of a calibration curve for components of a protein mixture relative to the fastest migrating component. The plot shows log(Molecular Weight) versus the relative migration of the protein components.

In addition to the separation of components of a mixture of biomolecules, the method of the present invention is also useful for molecular weight determinations of a selected biomolecule. Example 3B describes the generation of a molecular weight calibration curve based on the relative migration of known protein standards to a selected molecular weight standard. FIG. 10 shows the calibration curve of log(MW) versus the migration of the protein standards relative to $\alpha$-lactalbumin (the selected reference standard). Any number of compounds having a known molecular weight and charge can be used as the reference standard to establish relative migration: for example, charged organic molecules; dyes; nucleic acids; proteins, and other charged biomolecules. In practice, the migration of the compound having unknown molecular weight is determined relative to the selected reference standard, such as $\alpha$-lactalbumin, and the molecular weight is then determined by comparison to a standard curve.

Figure 11:
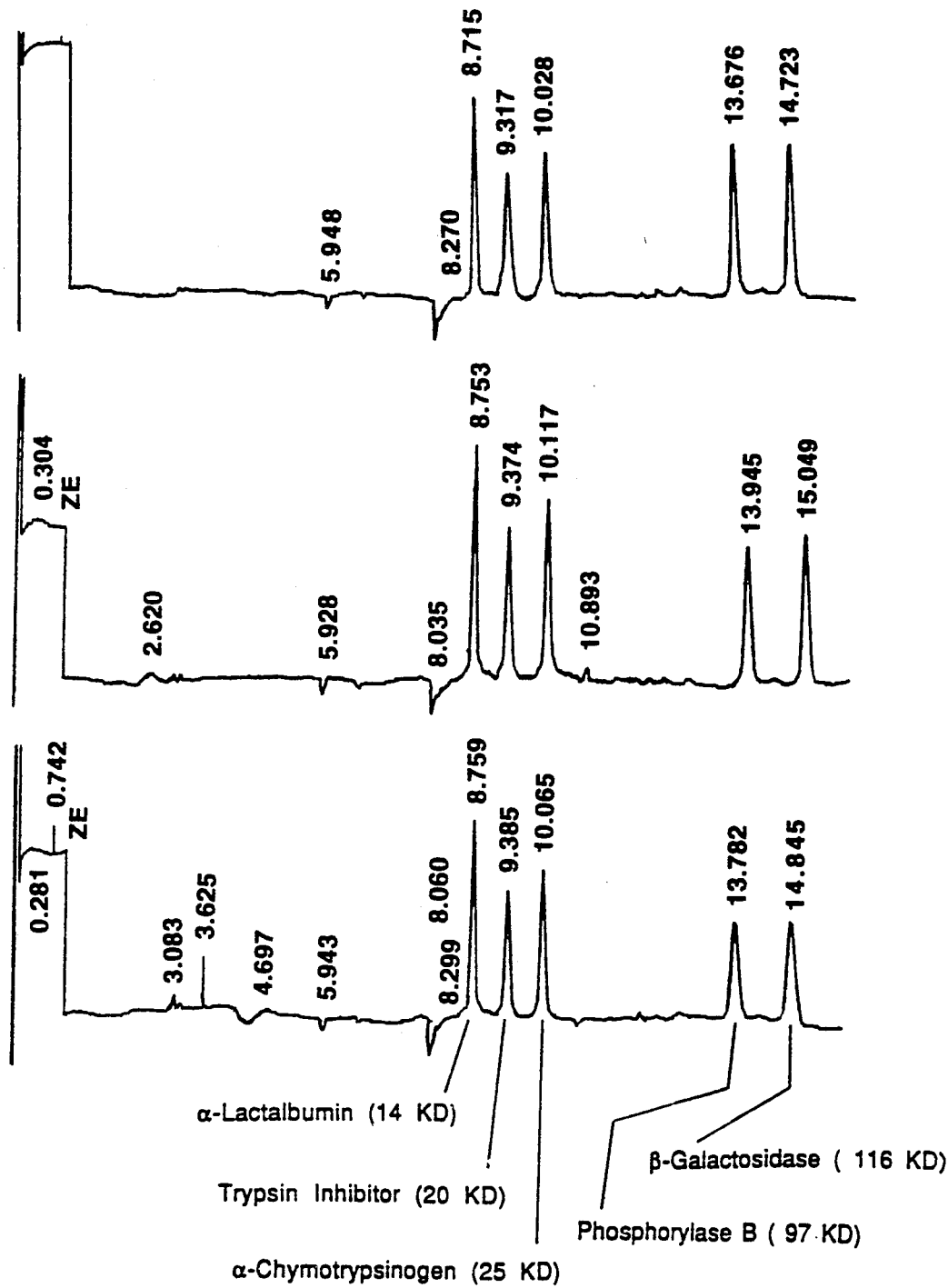
FIG. 11 shows the results of 3 runs sampled from 50 sequential runs of protein separations using the polymer solution of the present invention, where the capillary tube was flushed between runs only with the polymer solution.

Example 3C demonstrates the reproducibility of the method of the present invention. A 3% w/v acrylamide/TEDMED copolymer solution was used for the separation of a mixture of protein standards. Fifty sequential runs were performed using the same mixture of proteins. Between each run the capillary was flushed using the acrylamide/TEMED copolymer solution. The separation results are shown in FIG. 11 for runs 1, 30 and 50. As can be seen from FIG. 11, separation of the components of the protein mixture is very reproducible by the method of the present invention and does not require complicated washing of the capillary (such as with water and NaOH) between each sample run.

Figure 15:
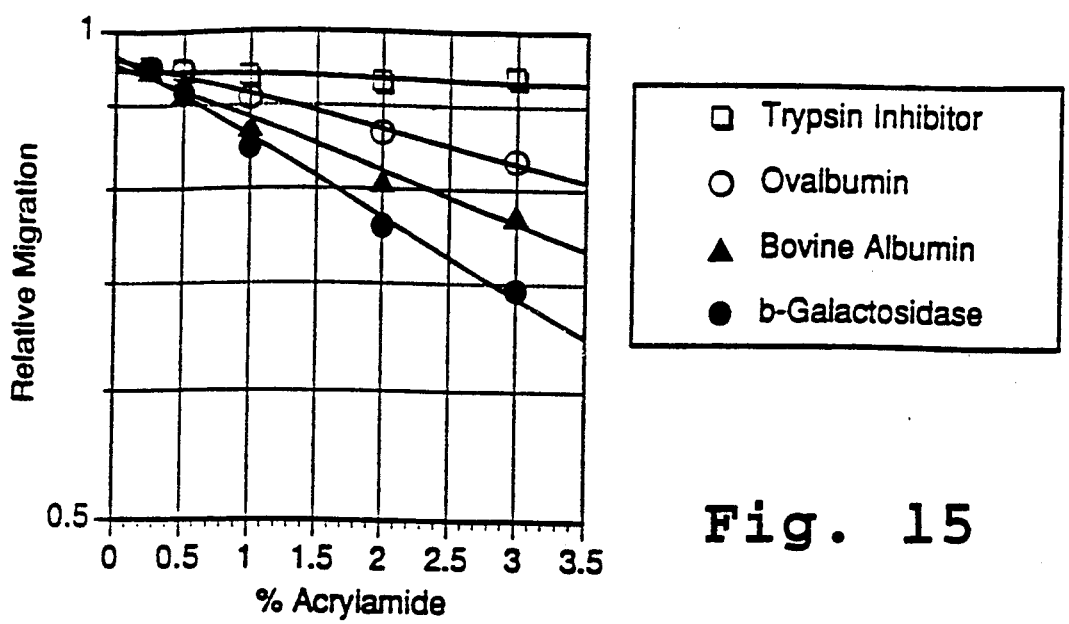
FIG. 15 shows the plot of relative migration times of proteins in a protein mixture, relative to the fastest migrating component, versus % polyacrylamide over a range of % polyacrylamide values (Ferguson Regression Analysis).

In Example 3D the effect of changing the percent concentration of polymer/copolymer in the solution on the relative migrations of biomolecules was examined. As the percent concentration of the polymer/copolymer changes, the differences in relative migration between the protein standards changes as well (FIG. 15). The slope of the lines in FIG. 15 for each protein standard are proportional to molecular weight, indicating that the polymer/copolymer solution is providing a true sieving matrix. Also, this method is another way to determine molecular weight for a given biomolecule: compare the slope of the line for an unknown biomolecule to a plot of the slopes of the lines of the molecular weight standards. The relative migration in FIG. 15 is the rate of migration of a particular protein relative to the migration of $\alpha$-lactalbumin, i.e., the migration time of $\alpha$-lactalbumin divided by the migration time of each standard protein.

Figure 12:
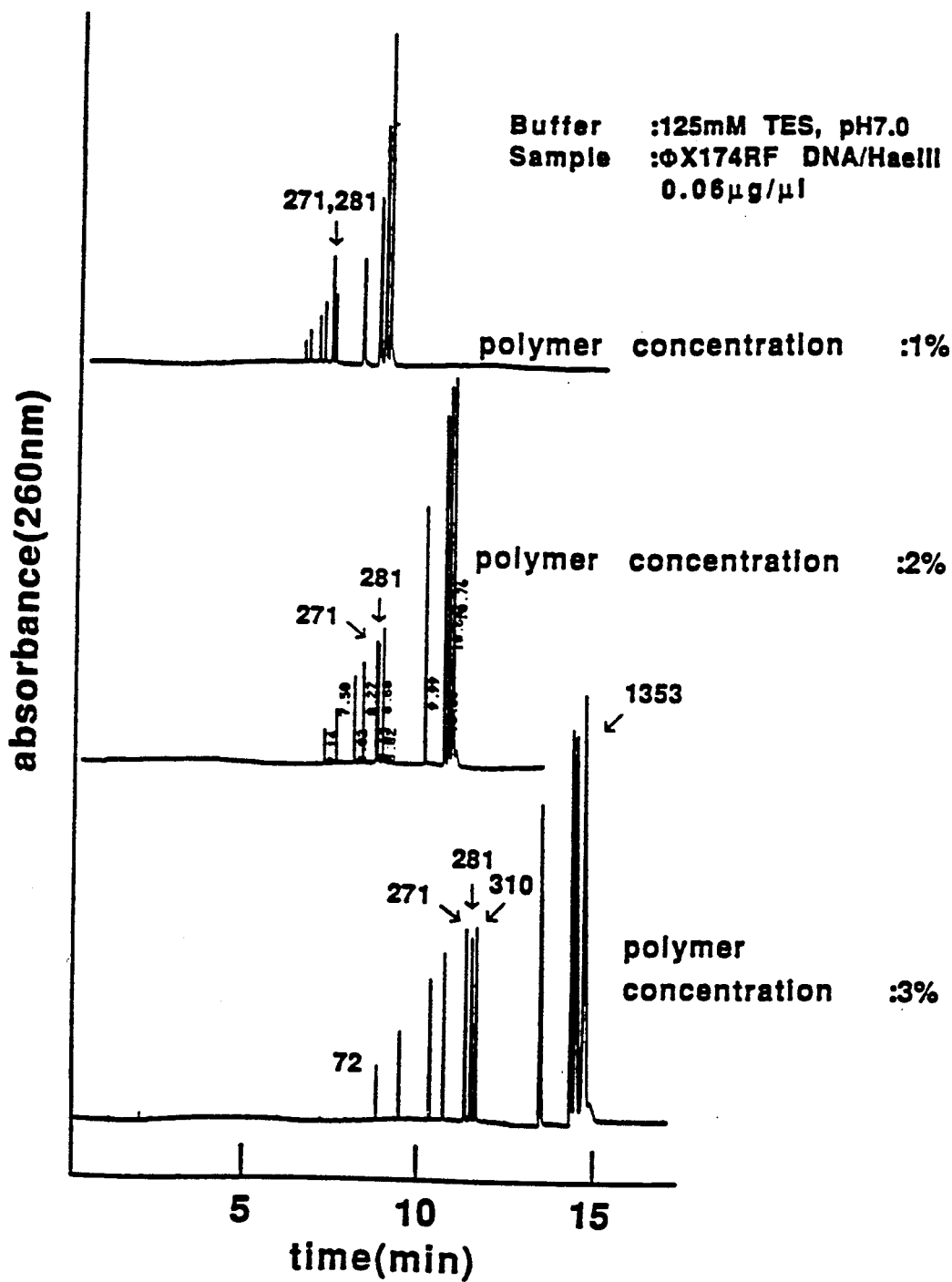
FIG. 12 shows the separation of double-stranded DNA molecules a cationic copolymer solution of the present invention at 1, 2, and 3% (w/v).

Example 4 demonstrates the separation of DNA fragments in a mixture of restriction digest fragments. $\phi$X174 RF HaeIII digest fragments were separated by the method of the present invention using polyacrylamide made with TEMED at 0.24 percent charge. There are 11 $\phi$X174 RF HaeIII digest fragments ranging in size from 72 to 1353 base pairs. FIG. 12 shows the resulting electropherograms for three copolymer concentrations 1, 2 and 3%. The data in FIG. 12 illustrates the property of the method of the present invention that increasing the percent concentration of the polymer/copolymer affects the separation ability of the technique. As can be seen in FIG. 12, as copolymer concentration increases the resolution of the peaks corresponding to the $\phi$X174 RF HaeIII 271 and 281 base pair fragments improves: at 2% they are starting to separate and at 3% percent the peaks are well resolved. This example illustrates how manipulating the percent concentration of the polymer in solution affects resolution.

Optimization of Separation Conditions

The characteristics of polymers useful in the present method for the adjustment of electroosmotic flow and molecular sieving in capillary electrophoresis include the following:

1. an electrolyte solution containing 0.05 to 30% weight to weight (w/w) of a non-cross-linked, hydrophilic polymer or copolymer solution containing at least one polymer or copolymer species;
2. where the polymer or copolymer species has a molecular weight between 20 and 5,000 kilodaltons; and 3. where the polymer or copolymer species has a percent charge of between 0.01 to 1.0% as measured by the molar percent of charged monomer subunits to the total polymer subunits, where the charged monomer subunits have the charge opposite to the wall charge at a selected electrophoresis pH.

For any selected polymer, copolymer, or mixture thereof, the percent charge value can be optimized by selecting a range of percent charge values essentially as described in Example 2 to discover the value for which electroosmotic flow is preferentially reduced to less than $2 \times 10^{-5}$. A further test of a selected polymer or copolymer solution is the separation of a target biomolecule sample. The % (w/w) polymer/copolymer in solution should be adjusted to obtain separation of the components of the selected mixture of biomolecules (for example, as shown with the above-described protein or DNA mixture). The solution should resolve components on the basis of size of the target biomolecule.

In addition to the use of polymers or copolymers bearing specific % charges, or in solutions at selected % (w/w) the rates of fragment migration may be selectively adjusted by:

a. Changes in the electric field strength. Migration times and to some degree resolution may be adjusted by performing the separation at about 100 to 400 V/cm.

b. Changes in the solution pH. Biomolecules, particularly proteins, may assume different net charge at different pH values. By adjusting the pH of the polymer solution between about pH 4 to 10, the relative migration rate may be altered.

c. Changes in temperature. Migration times and resolution may be changed by performing separations at temperatures of about 10° to 60° C. Lower temperature generally improves resolution.

d. Changes in buffer type concentration or ionic strength. For any given buffer species used in the polymer/copolymer solution, there exists an optimum range of concentration for maximum resolution. Band-broadening may occur at a too low concentration (low ionic strength) or band-broadening may occur at too high of a ionic strength. In particular, zwitterionic buffers improve resolution and reduce background UV absorbance variations.

e. Addition of surfactants to buffer. The incorporation of hydro- or fluorocarbon surfactants with neutral, positive, or negatively charged head groups will selectively alter migrations of proteins. In particular, the presence of sodium dodecylsulfate (SDS) in buffer results in migrations proportional to the protein molecular weight.

Summarizing the above, the present invention provides a variety of parameters which may be selectively varied to enhance biomolecule fractionation. The biomolecule migration rates can be selectively altered by changing the nature of the polymer and its concentration, the pH of solution, separating temperature and field strength, and buffer composition. For nucleic acids, the migration rates can be selectively changed by complexing the fragments with a non-ionic intercalating agent, such as ethidium bromide or acridine orange.

VI. Pulsed Field Separation

The electrophoretic methods described above were carried out under a constant-voltage field. In accordance with another aspect of the invention, the fractionation of biomolecules, in particular, nucleic acid fragments, can be enhanced by carrying out the electrophoretic separation under a pulsed-voltage field, at a frequency effective to selectively enhance separation within a given fragment size range.

In theory, the migration rate behavior of nucleic acid fragments in a pulsed field may be governed by two size-related effects. The first effect is a resonance effect involving the fragment's rotational modes and the frequency of the electric field. Table 1 below shows rotational and stretching resonance frequencies which have been calculated for 100, 1,000, and 10,000 basepair duplex DNA fragments. The rotational resonance frequencies in Hz were calculated on the basis of a prolate ellipsoid model of the duplex molecule (Mathew, et al.; Cantor, et al.).

TABLE 1

| Model | Fragment Size (base pairs) | | |
|---|---|---|---|
| | 100 | 1000 | 10,000 |
| Prolate Elipsoid (rotational motion) | $9.9 \times 10^4$ | $1.6 \times 10^2$ | $2.2 \times 10^{-1}$ |
| Viscoelastic (stretching motion) | $3.8 \times 10^5$ | $8.1 \times 10^3$ | $1.7 \times 10^2$ |

A strong rotational resonance effect predicts that the migration rates of fragments in resonance with the electric field will be preferentially slowed with respect to the migration rate in a time-invariant field. This is because a molecule in rotational resonance with the electric field would be expected to be, on average, least favorably oriented for migration in the direction of the field when the electric field is greatest. Larger molecules, because of their slower rotational times, would be expected to be less perturbed from their field-oriented positions at each voltage-pulse cycle; smaller molecules, with their faster response times, would more quickly reorient in the direction of the field. Thus, if rotational resonance effects are dominant, it should be possible to slow the migration of resonance species during electrophoresis relative to the rate of migration of non-resonance species.

Figure 9:
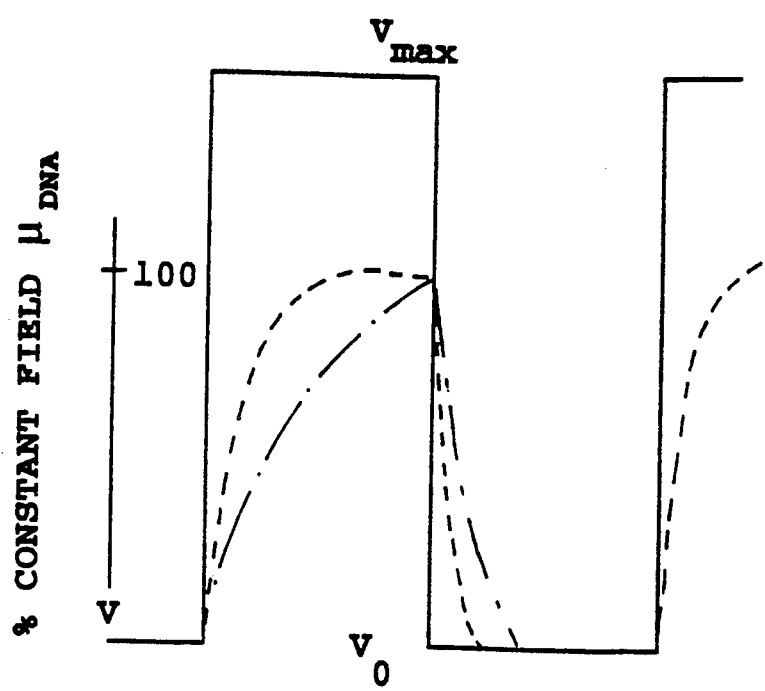
FIG. 9 shows hypothetical velocity curves for relatively small (dash lines) and relatively large (dash-dot lines) nucleic acid fragments, in relation to an applied square-wave voltage having a pulse width and a maximum voltage $V_{max}$.

The second size-dependent effect which may be expected in a pulsed field is an inertial effect due to the acceleration and deceleration of fragments in a fluid with each voltage pulse. This effect is illustrated in FIG. 9, which shows hypothetical velocity curves for relatively small (dash lines) and relatively large (dash-dot lines) nucleic acid fragments, in relation to an applied square-wave voltage having a pulse width and a maximum voltage $v_{max}$. The maximum velocity which the fragments should reach is the terminal or steady-state velocity of the fragments in a constant voltage field of potential $v_{max}$, i.e., 100% of the constant field migration rate.

As seen from the figure, smaller fragments are expected to reach terminal velocity more rapidly than large ones after application of the voltage pulse, but to decelerate to zero voltage substantially at the same rate when the voltage pulse ends. Since the total distance traveled by each fragment during a voltage pulse is just the integral of the velocity curve, the migration rates of larger fragments are expected to be preferentially decreased in a pulse-voltage field. It can also be appreciated that the higher the pulse frequency and shorter pulse duration, the smaller the fragment size which can be preferentially retarded in its migration rate, since the effect of any lag in the velocity curve becomes accentuated at short pulses.

In some mixtures of biomolecules, in particular nucleic acid fragments where it is desired to fractionate species in different size ranges, the variables discussed above—including solution pH, and polymer type and concentration, and field frequency—may be selectively varied during the electrophoretic run to enhance fragment resolution. For example, an electrophoretic separation may be carried out under a constant field or low frequency initially, to resolve larger size fragment, then switched to a higher frequency to improve resolution of smaller size fragments. As another example, the pH or polymer concentration of the polymer solution can be continuously varied during an electrophoretic run, using a standard two-chamber mixing device to produce a continuous solution gradient which is drawn into the capillary tube.

VII. Utility

The fractionation method of the invention finds utility in any of a variety of applications mentioned above requiring size fractionation of biomolecules. These applications include electrophoretic separations of proteins, polypeptides, peptides and single and double strand nucleic acids, including restriction analysis of DNA.

Applications of the analysis of restriction digestion products include the following: analysis of restriction fragment length polymorphisms for genetic screening, confirming vector construction, identifying specific nucleic acid fragments on the basis of size and/or hybridization to nucleic acid probes, and fractionating single-strand fragments for chemical or enzymatic sequencing.

The following applications illustrate how the method may be used for restriction fragment analysis. In the restriction analysis example, it is desired to identify, from a mixture of genomic fragments, a restriction fragment which contains a target sequence of interest. After digesting the genomic mixture with a selected restriction enzyme or enzyme(s), the fragment mixture is combined under hybridization conditions with reporter-labelled probe capable of hybridizing with the target sequence. The probe preferably includes the complementary target sequence and a covalently bound probe, such as a fluorescent probe which can be readily detected by a fluorescence probe detector. The probe may be hybridized with the fragments, for example, by standard denaturation/renaturation conditions involving single-strand species, or bound to the fragments in duplex form by RecA catalyzed triplex formation.

After binding the probe to the fragments, the sample is fractionated according to present method. The detector is preferably operated in a dual-wavelength mode, in which UV absorption and fluorescence emission detection are carried out concurrently.

By the method of the present invention, proteins, polypeptides, and peptides, either in a denatured state, native state, or chemically modified, are separated according to their size or molecular weight by electrophoresis in a tube containing a polymer and/or copolymer electrolyte solution. When this solution is employed for separation by capillary electrophoresis, very rapid and high resolution molecular weight (MW) separations of SDS (sodium dodecylsulfate) denatured proteins are obtained (see FIGS. 6 and 7). By correlating relative migration times with molecular weights of standard proteins, the molecular weight of unknown proteins can be estimated.

High mass sensitivity and reproducible migration times are obtained by utilizing polymers or copolymers which have a percent charge in the range of approximately 0.01 to 1.0%, where the charge on the polymers or copolymers is opposite the charge on the inner surface of the capillary tubing. This combination serves to substantially reduce electroosmotic flow to below approximately $2 \times 10^{-5}$ cm$^2$/sec-V and to prevent adsorption of proteins during electrophoresis. Not all applications require reduction of electroosmotic flow to below $2 \times 10^{-5}$ cm$^2$/sec-V: substantial reduction of electroosmotic flow occurs at approximately $8 \times 10^{-5}$ cm$^2$/sec-V. The polymer solution used for separation is introduced into the capillary tube using moderate pressures found in conventional capillary electrophoresis equipment.

After separation of a sample containing biomolecules, the capillary is flushed with fresh polymer solution before analysis of the next sample. This step eliminates the possibility, when processing sequential samples, of contamination, or "ghost peaks" from previous samples. The ability to flush the system with fresh polymer solution is made possible by limiting the viscosity of the polymer solution.

The polymer or copolymer used in the separation solution has a molecular weight within the range of 20 and 5,000 kilodaltons. The molecular weight of this polymer is typically above a threshold value for entanglement which will exert a retardation to electrophoretic migration of the selected biomolecules, which is proportional to the molecular weight of the biomolecules (Grossman, U.S. patent application Ser. No. 07/731,771, herein incorporated by reference). The molecular weight of the polymer or copolymer in solution is below a value which results in a solution of high viscosity that cannot be introduced into a narrow capillary (less than 200 $\mu$M I.D.) using pressures found in conventional capillary electrophoresis equipment.

The polymer or copolymer electrolyte solution may also contain an organic or inorganic ion, used for pH control and optical stability, including the following: Organic acids (such as citric, acetic, formic) or zwitterionics (such as TES (N-tris[Hydroxymethyl]-2-aminoethanesulfonic acid) (Sigma), BICINE (N,N-bis[2-hydroxyethyl]glycine) (Sigma), ACES (2-[2-Amino-2-oxoethyl)-amino]ethanesulfonic acid) (Sigma)); Inorganic acids (such as phosphoric); and Organic bases (such as "TRIS" (Sigma)).

When performing denaturing separations, an anionic surfactant can also be added to the polymer or copolymer electrolyte solution. The anionic surfactant is typically a hydrocarbon or fluorocarbon sulfate (such as sodium dodecylsulfate (SDS)), sulfonic (such as sodium decanesulfonic), or a carboxylic (such as lauric acid). For example, an SDS denatured protein sample, diluted in water, can be injected electrokinetically into the capillary. Separations are usually completed in under 15 minutes when using about a 30 cm separation length and 200 V/cm field strength.

When employing on-column UV detection at wavelengths less than 240 nm, the zwitterionic buffers such as, ACES or TES (Sigma), in a separation solution containing polyacrylamide and SDS at pH 6 to 8, exerts a stabilization effect on the background UV absorbance. This stabilization permits repeatable and sensitive UV detection at 200 nm without excessive baseline sloping.

The use of a polymer or copolymer solution as described above for the capillary electrophoretic separation of proteins or nucleic acids by molecular weight is an advantage over conventional PAGE slab gel separations by providing (1) a shorter analysis time, (2) a totally automated separation and detection, (3) a quantitative analysis, (4) a non-destructive analysis of extremely small amounts of proteins or nucleic acids (picograms), and (5) a user convenient matrix (i.e., a pre-tested polymer solution and no solid gels to prepare).

In a solid gel matrix, ghost peaks are hard to eliminate. Also in solid gels, irreversibly-bound material in the matrix tends to interact with the biomolecules in subsequent separations, thus decreasing resolution. One advantage of the method of the present invention is that the separation matrix, i.e., the polymer/copolymer solution, can be replaced between each run. A further advantage of the present invention is that when electrokinetic injection is inefficient in introducing sample mass into the capillary, a hydrodynamic injection, accomplished by vacuum or positive pressure, may be used to move a mass of sample into the capillary.

The low-charge-containing polymers and copolymers used in the method of the present invention act as coatings of the inner charged surface wall of the capillary tube and as molecular sieving matrices for biomolecules.

The following examples illustrate, but in no way are intended to limit the present invention.

EXAMPLE 1 Synthesis of Charged Polymers or Copolymers A. Copolymer of Acrylamide and TEMED The addition of varying amounts of TEMED (N,N,N',N'-Tetramethyl-ethylenediamine, (Aldrich Chemical Co.) to the ammonium persulfate (Aldrich Chemical Co.) initiated polymerization of acrylamide (Aldrich Chemical Co.) results in the production of polyacrylamides with varying molecular weights (see viscosity data, FIG. 4) and percent charges (see EOF data, FIG. 4). The following example illustrates the synthesis of polyacrylamide in which the molar percent of TEMED to acrylamide is 0.24%. The molar percent of TEMED can be increased or decreased by increasing or decreasing the concentration of the TEMED in the solution which is added to the polymerization mixture in this example.

To 500 mL of deionized water contained in a 2 L flask is added 100 g of acrylamide. This solution is stirred for 15 minutes at 50° C. with constant but gentle bubbling of helium. Add 400 mL of methanol (Burdick and Jackson, HPLC grade) and continue stirring for an additional 15 minutes with a water-cooled condenser attached to the reaction flask. Add 10 mL of 10% (v/v) TEMED in water and stir for 2 minutes. Add 10 ml of 10% (w/v) of ammonium persulfate and allow polymerization to progress for 2 hours with stirring.

Pour the clear, viscous liquid reaction mixture into a 3 L polypropylene beaker. With constant manual stirring, slowly add 500 mL of methanol. The resulting precipitate of solid, white clump(s)of polyacrylamide are allowed to settle to the bottom of the beaker. Decant the supernatant to waste. Add 500 mL of methanol to the beaker and manually squeeze the clump(s) with a glass rod and swirl methanol around the clump(s) in order to wash residual material into the supernatant which may appear cloudy. Allow the solid clump to settle and decant supernatant to waste. Repeat this methanol washing procedure three times or more until the supernatant appears relatively clear.

Break or cut the solid clump into pieces of about 1 cm×2 cm or smaller dimensions and place these pieces into polypropylene trays. The trays with the separated pieces are put into a vacuum oven (VWR 1430 or equivalent) and dried for 24 hours at 50°-60° C. at about 30" Hg vacuum (supplied by a Trivac D2A vacuum pump or equivalent connected to a cooled vapor trap). The dried pieces of polyacrylamide are ground to a granular powder in a micro-mill (Bel-Art, VWR Scientific) and stored desiccated in small vials until used to make a polymer solution.

B. Copolymer of Acrylamide and DADMAC

The addition of varying amounts of DADMAC (diallydimethylammonium chloride, Aldrich Chemical Co.) to the Ammonium persulfate initiated polymerization of acrylamide results in the production of polyacrylamides with varying molecular weights (see viscosity data, FIG. 5) and percent charge (see EOF data, FIG. 5). The following example shows how to make a polyacrylamide with a molar percent of 0.05 DADMAC to acrylamide. The molar percent of DADMAC may be increased or decreased by increasing or decreasing the concentration of DADMAC in the solution used in this example.

The synthesis and recovery of polyacrylamide is carried out as specified in the above example A.) except in place of TEMED, once would substitute 10 mL of 1.14 (w/v) DADMAC in water.

C. Conversion of Amide Groups in Polyacrylamide to Amines

The conversion of a small percentage of amide groups in polyacrylamide to the corresponding charged amine group is accomplished using the well-known Hofmann degradation (Jen). A solution of 40 parts of 5.25% sodium hypochlorite and 2.3 parts of sodium hydroxide is added over 20 minutes to 355 parts of a 20% solution of polyacrylamide in water. The polyacrylamide is prepared as described above in A.) without the addition of TEMED. With a temperature of 30° to 37° C. the reaction is held for 30 minutes. The reaction solution is neutralized with HCL to pH 6.9. The polyacrylamide is recovered by precipitation as described above in A.). The percent charge on the polyacrylamide is increased or decreased by increasing or decreasing the total reaction time.

D. Grafting Copolymer of Acrylamide and DADMAC onto Dextran

Acrylamide copolymer is grafted onto a backbone of dextran using a procedure similar to (McCormick). An aqueous solution of 1.25 g dextran, 8.165 g acrylamide, and 0.66 g DADMAC is stirred under helium at 25° C. for 30 minutes. Ten mL of 0.05 N nitric acid solution containing 0.0274 g ceric ammonium nitrate is added to start polymerization. After 3 hours the graft copolymer is recovered by precipitation as described in A.). The percent charge is increased or decreased from this example (i.e., 0.05%) by increasing or decreasing the amount of DADMAC added to the reaction mixture.

E. Polymer or Copolymer Solutions.

The polymer or copolymer is added to the desired buffer solution (w/v). The solution is then mixed by gentle rotation for approximately two hours after which the solution is filtered through a 0.45 micron filter. The solution is placed in a vacuum oven for degassing at 30° C. and 29 inches of Hg for 15 minutes. The solution is then introduced into the detector-side and buffer-side reservoirs of the capillary electrophoresis instrument.

EXAMPLE 2 The Effect of Charged Polymer or Copolymers on Specific Viscosity and Electroosmotic Flow Capillary electrophoresis was carried out using an ABI Model 270 Capillary Electrophoresis System. The system includes a built-in high-voltage DC power supply capable of voltage settings up to 30 KV. The capillary tube used in the system is a fused silica capillary tube 50 cm long with a 55 μm i.d. and 350 μm o.d. obtained from Polymicro Technologies (Phoenix, Ariz.).

The marker used to indicate the rate of electroosmotic flow ($V_{eo}$) was the neutral compound, mesityl oxide, which has a UV absorbance at 200 mm. The electrophoretic system was run at a voltage setting of about +10 kV (about +200 V/cm) through the run at a temperature of 30° C. UV detection was with a built-in 783 UV detector designed for capillary tube detection. The detector output signal was integrated and plotted on a Spectrophysics Sp4400 integrator/plotter.

Fresh capillary surface was routinely prepared by flushing the capillary successively with 5-10 capillary volumes of 1.0 N NaOH, 3-5 volumes 0.1 N NaOH, and finally 3-5 volumes of polymer solution. Solutions are drawn through the capillary by vacuum using a built-in regulated vacuum system at the anodic end.

In general, after equilibration with the chosen polymer/copolymer electrolyte solution, 2-5 nl of neutral marker (mesityl oxide) is injected into the capillary by virtue of vacuum applied at the detector end; the marker is used to measure electroosmotic flow. The field is applied (+200 v/cm) and the time (t, seconds) for the marker to migrate to the detector (30 cm) is recorded.

Electroosmotic flow mobility (EOF) is calculated as:

$$EOF = \frac{30 \text{ cm}}{200 \text{ V/cm}} \cdot \frac{1}{t}$$

Biomolecules are typically electrokinetically injected. For example, a sample of the biomolecules, at about 0.01 milligrams per ml., is electrokinetically injected at −5 kV for 10 secs following electrokinetic injection of the reference marker at −5 kV for 2 seconds. Appropriate voltage is then applied to complete the run, typically of about −10 kV up to approximately −20 kV, depending on the particular separation.

A. Acrylamide and TEMED Copolymer.

Mixtures of acrylamide and tetramethylethylenediamine (TEMED) were formed as described in Example 1 at the TEMED to acrylamide monomer ($[AA_m]$) percent shown at the bottom of FIG. 4. The copolymer solution was formed in a buffer consisting of 50 mM ACES, pH 7.0 and 0.2% SDS. This buffer or other suitable electrolyte solutions can be used for formation of the copolymer electrolyte solution. The concentration of polyacrylamide was 2% (w/w). The viscosity of the copolymer electrolyte solution was determined using a capillary viscometer, as described above. The copolymer electrolyte solution was pulled by vacuum through the capillary tube as described above. Two to five nanoliters of neutral marker (mesityl oxide) were injected into the capillary by virtue of vacuum applied at the cathodic end. A voltage of 200 v/cm was applied. Electroosmotic flow (EOF) was determined as the mobility of the marker calculated in $cm^2/sec$-V.

The results are presented in FIG. 4. As can be seen from FIG. 4, at TEMED/$[AA_m]$ values in the range of approximately 0.05% to 0.5%, EOF mobility is reduced to less than $2 \times 10^{-5}$ $cm^2/sec$-V: an EOF mobility value of approximately $2 \times 10^{-5}$ $cm^2/sec$-V reflects a very low level of electroosmotic flow.

B. Acrylamide and DADMAC Copolymer

Mixtures of acrylamide and diallyldimethylamoniummchloride (DADMAC) were reacted as described in Example 1 at the DADMAC to acrylamide monomer ($[AA_m]$) percent shown at the bottom of FIG. 5. The copolymer solution was formed in a buffer consisting of 50 mM ACES, pH 7.0 and 0.2% SDS. This buffer or other suitable electrolyte solutions can be used for formation of the copolymer electrolyte solution. The concentration of acrylamide copolymer was 2%. The viscosity of the copolymer electrolyte solution was determined using a capillary viscometer, as described above. The copolymer electrolyte solution was pulled by vacuum through the capillary tube as described above. Two to five nanoliters of neutral marker (mesityl oxide) were injected into the capillary by virtue of vacuum applied at the cathodic end. A voltage of +200 v/cm was applied. Electroosmotic flow (EOF) was determined as the mobility of the neutral marker calculated in $cm^2/sec$-V.

The results are presented in FIG. 5. As can be seen from FIG. 5, at DADMAC/$[AA_m]$ values in the range of approximately 0.05% to 0.26%, EOF mobility is reduced to less than $2 \times 10^{-5}$ $cm^2/sec$-V: an EOF mobility value of approximately $2 \times 10^{-5}$ $cm^2/sec$-V reflects a very low level of electroosmotic flow.

EXAMPLE 3 Separation of Sample Polypeptides A. Protein Separation.

A mixture of the following proteins was purchased from Sigma (St. Louis Mo.): α-lactalbumin (14 kd), soybean trypsin inhibitor (20 kd), egg albumin (45 kd), bovine albumin (66 kd), and β-galactosidase (116 kd). The proteins in the mixture were SDS-denatured by standard procedures (Ausubel, et al.). Briefly, the protein at 1.0 mg/ml in 1% SDS/1% mercaptoethanol were heated in boiling water for 15 minutes. The proteins were diluted with water to 0.02 mg/ml before analysis.

Mixtures of acrylamide and diallyldimethylamoniummchloride (DADMAC) were prepared as described in Example 1 at the DADMAC to acrylamide monomer ($[AA_m]$) percent shown in FIGS. 6 and 7. The copolymer solution was formed in a buffer consisting of 50 mM ACES, pH 7.0, (Sigma) which contained 0.2% sodium dodecyl sulfate (SDS). The concentration of the linear copolymer polyacrylamide/DADMAC in solution was 2% (w/v). The copolymer electrolyte solution was pulled by vacuum through the capillary tube as described above and the cathodic end of the capillary was placed in the sample mixture. About 1-2 nanograms of protein was injected into the capillary by virtue of a field strength of −100 V/cm for 10 seconds. With the capillary end in the buffer reservoir, a field strength of −200 V/cm was applied. The separation was run at 30°

C. and proteins detected at 200 nm. The capillary tube had an inner diameter of 55 μM and an effective separation length of 28 cm.

Electropherograms showing the results of CE for the separation of the components of the protein mixture, performed with DADMAC/[AA$_m$], are shown in FIGS. 6 and 7.

B. Size Calibration

The above-described protein mixture was separated essentially as described above, using a TEMED/[AA$_m$] of 0.24% at a concentration of the linear copolymer polyacrylamide/TEMED in solution of 3% (w/v). The log(MW) was plotted versus the migration of the protein standards relative to α-lactalbumin (migration time of α-lactalbumin divided by the migration time of the protein peak in question) for each protein in the mixture and the resulting calibration curve is shown in FIG. 10.

C. Reproducibility

The reproducibility of the method of the present invention was demonstrated by repeated sample injections, under the above conditions, where the capillary was flushed with the copolymer solution for 10 min at 20" Hg between each sample run. All sample proteins were obtained from Sigma. The concentration of the linear copolymer polyacrylamide/TEMED in solution was 3% w/v. The TEMED/[AA$_m$] concentration was 0.24%. Fifty sequential sample runs were performed and the separation results are shown in FIG. 11 for runs 1, 30 and 50.

D. Ferguson Regression Analysis

The relative migrations of each of the proteins in the above-described protein mixture were determined relative to the migration of α-lactalbumin at a number of percent copolymer concentrations. The copolymer used in this analysis was TEMED/[AA$_m$] at 0.24% over the range of concentrations of the linear copolymer polyacrylamide/TEMED in solution shown in FIG. 15. The CE conditions were as described above.

EXAMPLE 4 Separation of Sample Nucleic Acids

φX174 RF digested with HaeIII was purchased from Bethesda Research Laboratories ((BRL) Gaithersburg Md.). HaeIII restriction digestion of φX174 RF yields 11 double-stranded DNA fragments in the size range of 72 to 1353 base pairs. The sample was diluted to 0.06 micrograms per microliter. Acrylamide and TEMED were prepared as described in Example 1 at 0.24 molar percent TEMED. The copolymer solution was formed in a buffer consisting of 125 mM TES (Sigma), pH7.0. The concentrations of the linear copolymer polyacrylamide/TEMED used for nucleic acid separation are shown in FIG. 12 (1, 2 and 3%). The copolymer electrolyte solution was pulled by vacuum through the capillary tube as described above and the cathodic end of the capillary was placed in the sample mixture. About 1-2 nanograms of the DNA restriction digest mixture was injected into the capillary by virtue of a field strength of −100 V/cm for 10 seconds. With the capillary end in the buffer reservoir, a field strength of −200 V/cm was applied. The separation was run at 30° C. and the DNA fragments detected by absorbance at 260 nm. The capillary tube had an inner diameter of 55 μM and an effective separation length of 28 cm.

An electropherogram showing the results of CE for the separation of the components of the DNA fragment mixture, performed with TEMED/[AA$_m$], are shown in FIG. 12.

While the invention has been described with reference to specific methods and embodiments, it will be appreciated that various modifications and changes may be made without departing from the invention.

It is claimed:

1. A method of separating biomolecules in a sample comprising
    preparing a capillary tube with two ends, where the capillary tube (i) has charged chemical groups on its inner wall surface, and (ii) is filled with an electrolyte solution containing 0.05 to 30% weight to weight (w/w) of a non-cross-linked, hydrophilic polymer or copolymer solution containing at least one polymer or copolymer species having (a) a molecular weight between 20 and 5,000 kilodaltons, and (b) a percent charge of between 0.01 to 1.0% as measured by the molar percent of charged monomer subunits to the total polymer subunits, where said charged monomer subunits have the charge opposite to the wall charge at a selected electrophoresis pH,
    immersing the ends of the tube in anodic and cathodic reservoirs containing an electrolyte solution,
    introducing a sample containing the biomolecules to be separated into one end of the tube, and
    applying an electric field across the reservoirs with a polarity effective to fractionate said biomolecules in the sample.

2. The method of claim 1, where the polymers or copolymers are selected from the group consisting of polyacrylamides, polyoxides, polyethers, vinyl polymers, cellulose polymers, acrylic polymers, and natural gums and polysaccharides, where said polymers or copolymers have been modified to contain a specified percent charge.

3. The method of claim 2, where the polymers or copolymers are polyacrylamides selected from the group consisting of polyacrylamide and polymethacrylamide.

4. The method of claim 2, where the polymers or copolymers are polyoxides selected from the group consisting of polyethyleneoxide and polypropylene oxide.

5. The method of claim 2, where the polymers or copolymers are polyethers and the polyether is a polyvinylmethylether.

6. The method of claim 2, where the polymers or copolymers are vinyl polymers selected from the group consisting of polyvinylpyrollydine, polyvinylalcohol, and polyvinylacetate.

7. The method of claim 2, where the polymers or copolymers are natural gums or polysaccharides selected from the group consisting of xanthans, dextrans, agar, guar, and starches.

8. The method of claim 2, where the polymers or copolymers are cellulose polymers selected from the group consisting of methylcellulose, hydroxyethylcellulose, hydroxylpropylcellulose, and hydroxypropylmethylcellulose.

9. The method of claim 2; where the polymers or copolymers are acrylic polymers selected from the group consisting of polyhydroxyethyl-methacrylate and polyethylene glycol monomethacrylate.

10. The method of claim 1, wherein the polymer or copolymer solution contains a homopolymer.

11. The method of claim 1, wherein the polymer or copolymer solution contains a copolymer.

12. The method of claim 1, wherein the polymer or copolymer molecules contain at least one charged group which has a charge selected from the group consisting of primary amines, secondary amines, quaternary amines, carboxylic acids, sulfonic acids, phosphoric acids, sulfuric acids, and phosphonic acids.

13. The method of claim 1, wherein the polymer or copolymer molecules contain at least one charged group selected from the group consisting of primary amines, secondary amines, and quaternary amines, and at least one charged group selected from the group consisting of carboxylic acids, sulfonic acids, phosphoric acids, sulfuric acids, and phosphonic acids.

14. The method of claim 1, wherein the polymer is a copolymer of acrylamide and diallyldimethylammoniumchloride (DADMAC) and said copolymer has a molecular weight between about 200 and 600 kd, and the polymer molecules contain 0.05 to 0.5% of the quaternary amine N,N-dimethyl-3,5-methylene piperidine per subunit acrylamide.

15. The method of claim 1, wherein the polymer is a copolymer of acrylamide and tetramethylethylenediamine (TEMED), and said copolymer has a molecular weight between about 100 and 500 kilodaltons, and the polymer molecules contain 0.02 to 0.4% of the tertiary amine tetramethylethylenediamine per subunit acrylamide.

16. The method of claim 1, wherein the concentration of polymer molecules containing a charge opposite the wall charge is sufficient to non-covalently coat the wall surface and significantly control and reduce electroosmotic flow to less than about $2 \times 10^{-5}$ cm$^2$/sec-V.

17. The method of claim 1, which further includes detecting the presence of separated biomolecules in the electrophoresis capillary tube by measuring electrochemical, optical or radioisotopic properties of the biomolecules in the tube.

18. The method of claim 1, wherein said biomolecules are selected from the group consisting of proteins, polypeptides, and peptides.

19. The method of claim 18, where said biomolecules have a net positive or negative charge at the pH of the electrophoresis medium.

20. The method of claim 18, where said biomolecules have been denatured with sodium dodecylsulfate and sodium dodecylsulfate is present in the electrolyte solution.

21. The method of claim 1, wherein said biomolecules are nucleic acid fragments.

22. The method of claim 21, where said biomolecules are single or double stranded.

23. The method of claim 22, wherein the fragments are double-stranded nucleic acids, and said differential migration is adjusted by the addition of an intercalating agent to the fragments, to increase preferentially the migration rates of smaller molecular weight fragments through the polymer solution.

24. The method of claim 23, wherein the intercalating agent is selected from the group consisting of ethidium bromide and acridine orange.

25. The method of claim 21, for use in performing restriction digest analysis of a DNA sample, which further comprises digesting the sample with one or more selected restriction endonucleases.

26. The method of claim 1, wherein said biomolecules are selected from the group consisting of linear, branched, native and chemically modified oligosaccharides.

27. A filled capillary tube for use in capillary electrophoresis, comprising a capillary tube having charged chemical groups on its inner wall surface, and filled with an electrolyte solution containing 0.05 to 30% weight to weight (w/w) of a non-cross-linked, hydrophilic polymer or copolymer solution containing at least one polymer or copolymer species having (a) a molecular weight between 20 and 5,000 kilodaltons, and (b) a percent charge of between 0.01 to 1.0% as measured by the molar percent of charged monomer subunits to the total polymer subunits, where said charged monomer subunits have the charge opposite to the wall charge at a selected electrophoresis pH.

28. The tube of claim 27, wherein the polymers or copolymers are selected from the group consisting of polyacrylamides, polyoxides, polyethers, vinyl polymers, cellulose polymers, acrylic polymers, and natural gums and polysaccharides, where said polymers or copolymers have been modified to contain a specified percent charge.

29. The tube of claim 27, wherein the polymer or copolymer molecules contain a charged group which has a net charge selected from the group consisting of primary amines, secondary amines, quaternary amines, carboxylic acids, sulfonic acids, phosphoric acids, sulfuric acids, and phosphonic acids.

30. The tube of claim 27, wherein the polymer is a copolymer of acrylamide and diallyldimethylammoniumchloride (DADMAC) and said copolymer has a molecule weight between about 200 and 600 kd, and the polymer molecules contain 0.02 to 0.4% of the quaternary amine N,N-dimethyl-3,5-methylene piperidine per subunit acrylamide.

31. The tube of claim 27, wherein the polymer is a copolymer of acrylamide and tetramethylethylenediamine (TEMED), and said copolymer has a molecular weight between about 100 and 500 kilodaltons, and the polymer molecules contain 0.05 to 0.5% of the tertiary amine tetramethylethylenediamine per subunit acrylamide.

* * * * *